(12) United States Patent
Marsh

(10) Patent No.: US 7,597,720 B2
(45) Date of Patent: Oct. 6, 2009

(54) OXIDIZING HAIR COLOURANT COMPOSITIONS

(75) Inventor: Jennifer Mary Marsh, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 12/258,980

(22) Filed: Oct. 27, 2008

(65) Prior Publication Data

US 2009/0119852 A1 May 14, 2009

(30) Foreign Application Priority Data

Nov. 5, 2007 (EP) .................................. 07119957

(51) Int. Cl.
*A61Q 5/10* (2006.01)
(52) U.S. Cl. .................. 8/405; 8/406; 8/408; 8/410; 8/411; 8/412; 8/435; 8/584; 8/633
(58) Field of Classification Search ............... 8/405, 8/406, 408, 410, 411, 412, 435, 584, 633
See application file for complete search history.

(56) References Cited

U.S. PATENT DOCUMENTS

| | | | |
|---|---|---|---|
| 3,202,579 A | 8/1965 | Berth et al. | |
| 3,542,918 A | 11/1970 | Berth et al. | |
| 4,138,478 A | 2/1979 | Reese et al. | |
| 5,635,167 A | 6/1997 | Said et al. | |
| 7,179,302 B2 | 2/2007 | Boswell et al. | |
| 7,186,275 B2 | 3/2007 | Boswell et al. | |
| 2004/0055095 A1 | 3/2004 | McKelvey et al. | |
| 2004/0123402 A1 | 7/2004 | Marsh et al. | |
| 2004/0237218 A1* | 12/2004 | Marsh et al. | .................. 8/405 |

FOREIGN PATENT DOCUMENTS

| WO | WO98/27944 | 7/1998 |
|---|---|---|
| WO | WO02078661 | 10/2002 |

* cited by examiner

*Primary Examiner*—Eisa B Elhilo
(74) *Attorney, Agent, or Firm*—Melissa G. Krasovec

(57) ABSTRACT

The present invention relates to oxidizing hair colorant compositions comprising selected oxidative hair dyes and diethylene-triamine-penta-(methylenephosphonic acid). The compositions provide improved hair color tonality, root to tip evenness and reduced wash fade over time.

11 Claims, No Drawings

OXIDIZING HAIR COLOURANT COMPOSITIONS

FIELD OF THE INVENTION

The present invention relates to oxidizing hair colourant compositions comprising selected oxidative hair dyes and an amino-phosphonic acid type chelant. The compositions provide improved hair colour tonality, root to tip evenness and reduced wash fade over time.

BACKGROUND OF THE INVENTION

Melanin is a natural pigment found in hair. Melanin and hair-forming cells are naturally produced in the hair bulb at the root of the hair. As new cells are produced, the older ones are pushed upwards out of the skin to form the hair shaft, which is the part of the hair that can be seen above the scalp. Hair can be schematically described as being made of a center part called the cortex, which contains the melanin, and an outer layer called the cuticle. It is the cortex that gives the hair its special qualities such as elasticity and curl.

The hair shaft is composed of dead cells that have turned into a mixture of different forms of the hair protein, keratin. Keratin contains high concentrations of a particular amino acid called cystine. Every cystine unit contains two cysteine amino acids in different chains, which have come to lie near each other and are linked together by two sulphur atoms, forming a very strong chemical bond known as a disulphide linkage. This cross-linking by disulphide linkages between the keratin chains accounts for much of the strength of the hair.

Bleaching and dyeing (or coloring) of hair has become increasingly popular over the past years. Younger people may want to change the natural color of their hair to a more fashionable one, while older people may also use dyeing compositions to conceal gray hair. As people grow older, the production of melanin slows, giving more and more gray hair over time.

Melanin can also be purposely altered by chemical treatments to give lighter shades. The lightening is achieved by oxidizing the melanin pigments with an oxidizing composition, usually in alkaline solution. The oxidizing compositions (bleaches) comprise an oxidizing agent, usually hydrogen peroxide. Other suitable oxidizing agents include potassium, sodium and ammonium salts of perborate, percarbonate, persulfate and percarbamide.

Bleaches are also used during oxidative dyeing treatments. Oxidative (or "permanent") dye compositions comprise "precursor dyes" which are small molecules capable of diffusing into the hair. These molecules mainly belong to three classes of aromatic compounds: diamines, aminophenols and phenols. They are sufficiently small to diffuse in the hair shaft where, once activated by an oxidizing agent such as hydrogen peroxide, they further react with other precursors to form larger colored complexes. These compounds can be used in numerous combinations in order to provide a particular desired colour. Oxidative hair dye compositions commonly contain, in addition to the dye precursors and a source of peroxide, a variety of additional cosmetic and peroxide stabilizing agents.

In order to stabilize the hydrogen peroxide solution which, even at acetic pH, has a tendency to decompose rapidly in solution thereby affecting its storage stability, low levels of chelants are routinely used as stabilizers or preservatives in various oxidizing compositions. For example, EDTA (ethylenediaminetetraacetic acid) is commonly used as a stabilizer in hydrogen peroxide solution. Amounts as low as 0.1% by weight of the oxidizing composition are usually used to stabilize the oxidizing agent contained in said oxidizing compositions.

Oxidative hair colourant treatments generally provide acceptable immediate results. However, achieving the desired tonality for oxidative colourants is still difficult. For example to provide ash or blue tones to blondes or to provide red tones to auburn and burgundy shades is still particularly difficult. Moreover, these tonal shades suffer from the additional drawbacks regarding their low root to tip evenness, as well as a tendency to rapidly lose the given tonality during subsequent wash cycles. This is due in part to a combination of factors; namely that firstly the dyes typically providing the tonality are only used at low levels in comparison to the other dye levels used to provide a particular shade; secondly that these dyes also have a low initial uptake in the hair and thirdly that these dyes also tend to have a rapid wash fade profile.

It has now been surprisingly found that chelants having an amino-phosphonic moiety, in particular in combination with selected oxidative couplers improve the tonality delivered by these dyes. It is a further advantage of the present invention that the initial dye uptake and wash fade is also improved. Whilst not being bound by theory, it is believed that the improved tonality is due to the ability of the amino-phosphonate type chelants to be effective chelators in both the oxidised and non oxidised form.

Phosphonate type chelants have been described in the art. U.S. Pat. No. 4,138,478 discloses agents for reducing the damage to hair during bleaching and dyeing by the use of a water-soluble 3-amino-1-hydroxypropane-1,1-diphosphonic compound to protect the hair from damage by "nascent oxygen". Other protective compounds such as hydroxyethane-1,1 diphosphonic acid (HEDP) and ethylenediaminetetramethylene phosphonic acid (EDTMP) are disclosed at low levels in U.S. Pat. No. 3,202,579 and U.S. Pat. No. 3,542,918.

U.S. Pat. No. 3,542,918 describes certain phosphonates for the prevention of damage to hair upon dyeing. A dye cream ("based upon conventional oxidative dyes") and phosphates is disclosed. WO02078661 also describes oxidising compositions comprising a phosphonic acid type chelant and a conditioning agent for improved hair feel. WO98/27944 describes hair colouring compositions comprising oxidising agent and hair colouring agent having a pH of from 1 to 4.5 to provide colour, good wash fastness and reduced hair damage. Chelants are disclosed. U.S. Pat. No. 5,635,167 describes the removal of minerals from hair by the application of a chelating agent selected from amino acid type or polyphosphate or phosphonate type agents.

SUMMARY OF THE INVENTION

The present invention relates to a hair colouring composition comprising a) an oxidizing agent and b) at least one primary intermediate (developer) hair dye and at least one coupler hair dye selected from 4-amino-2-hydroxytoluene, 2-methyl-5-hydroxyethylaminophenol, 2,4-diaminophenoxyethanol, 6-hydroxybenzomorpholine, 1-napthol and mixtures thereof and c) diethylene-triamine-penta-(methylenephosphonic acid) (DTPMP).

The present invention also relates to a method of treating hair comprising the subsequent steps of:

i) contacting hair with a first composition comprising:

a) diethylene-triamine-penta-(methylenephosphonic acid) (DTPMP);

ii) contacting the hair immediately after step i) with a second composition comprising an oxidizing agent, a primary intermediate (developer) dye and at least one coupler dye selected from 4-amino-2-hydroxytoluene, 2-methyl-5-hydroxyethylaminophenol 2,4-diaminophenoxyethanol, 6-hydroxybenzo-morpholine, 1-napthol and mixtures thereof.

DETAILED DESCRIPTION OF THE INVENTION

While the specification concludes with claims which particularly point out and distinctly claim the invention, it is believed the present invention will be better understood from the following description.

As used herein the term "hair" to be treated may be "living" i.e. on a living body or may be "non-living" i.e. in a wig, hairpiece or other aggregation of non-living keratinous fibers. Mammalian, preferably human hair is preferred. However wool, fur and other keratin containing fibers are suitable substrates for the compositions according to the present invention.

All percentages are by weight of the total composition unless specifically stated otherwise. When more than one composition are used during a treatment, the total weight to be considered is the total weight of all the compositions applied on hair simultaneously (i.e. the weight found "on head") unless otherwise specified. All ratios are weight ratios unless specifically stated otherwise.

Amino-Phosphonic Acid Chelants

The term "chelant" (or "chelating agent" or "sequestering agent") is well known in the art and refers to a molecule or a mixture of different molecules each capable of forming a chelate with a metal ion. A chelate is an inorganic complex in which a compound (chelant) is coordinated to a metal ion at two or more points so that there is a ring of atoms including the metals. Chelants contain two or more electron donor atoms that form the coordination bonds with the metal ion.

It has been observed that the presence of redox metals such as copper and iron, which whilst only present in low levels of 5 to 100 ppm and calcium typically present at levels such as 4000 to 10000 ppm, in tap water used by consumers can effect the colour chemistry of oxidative hair dyes. These metals increase the rate of the formation of the dye due to the redox reaction with hydrogen peroxide from HO radicals. It has now been surprisingly found that diethylene-triamine-penta-(methylenephosphonic acid) (DTPMP) is effective at complexing the ow levels of copper and iron as well as calcium albeit not as strongly. In this manner whilst not being bound by theory it is believed that the use of diethylene-triamine-penta-(methylenephosphonic acid) (DTPMP) controls the rate of colour formation in the oxidative colour chemistry process.

According to the present invention, the oxidizing hair colourant compositions comprise from 0.01% to 5%, preferably from 0.25% to 3% more preferably from 0.25% to 1% of diethylene-triamine-penta-(methylenephosphonic acid) (DTPMP)

Dyes

According to the present invention the composition comprise at least one primary intermediate (developer) hair dye and at least one coupler hair dye selected from 4-amino-2-hydroxytoluene (AHT), 2-methyl-5-hydroxyethylaminophenol (PAOX), 2,4-diaminophenoxyethanol (DAPE), 6-hydroxybenzomorpholine, 1-napthol and mixtures thereof. According to the present invention the compositions comprise from 0.001 to 5%, preferably from 0.01 to 3%, more preferably from 0.01 to 2% of said coupler.

Suitable primary intermediate (developers) for use herein include methoxymethyl-p-phenylenediamine, 2,6-dichloro-4-aminophenol, 5-amino-2-ethyl-phenol, 2,5-toluenediamine sulphate, N-phenyl-p-phenylenediamine, p-phenyldiamine, p-methylaminophenol, N,N-bis(2-hydroxyethyl)-p-phenylenediamine, 5-methyl-o-aminophenol, 5-ethyl-o-aminophenol, 3-methyl-p-minophenol, hydroxyethyl-p-phenylenediamine, hydroxypropyl his (N-hydroxyethyl)-p-phenylenediamine, 1-hydroxyethyl 4,5-diamino pyrazole, 2,2'-methylenebis-4-aminophenol and mixtures thereof. According to the present invention the compositions comprise from 0.001% to 5%, preferably from 0.01% to 3%, more preferably from 0.01% to 2% of said primary intermediate (developers).

It has been surprisingly found that the combination of amino-phosphonate acid type chelants and derivatives thereof and certain primary intermediate (developers) and couplers improve the tonality delivered by these dyes. It is a further advantage of the present invention that the initial dye uptake and wash fade is also improved. Whilst not being bound by theory it is believed that the improved tonality is due to the ability of the amino-phosphonate type chelants to be effective chelators in both the oxidised and non oxidised form.

Additional Components

The compositions of the present invention may further comprise additional ingredients which include, but are not limited to, hair dyeing agents such as additional oxidative dye precursors, non-oxidative dyes, thickeners, solvents, enzymes, surfactants, conditioning agents, carriers, antioxidants, stabilizers, chelants, perming actives, perfume, reducing agents (thiolactic acid), hair swelling agents and/or polymers. Some of these additional components are detailed hereafter.

Hair Dyes

The hair colouring compositions of the present invention may in addition to the specified dyes comprise additional hair dye materials. Such compositions comprise oxidative hair dye precursors (known as developers or primary intermediates) that will deliver a variety of hair colors to the hair. These small molecules are activated by the oxidizing agent and react with further molecules to form a larger colored complex in the hair shaft. The precursors can be used alone or in combination with other precursors, and one or more can be used in combination with one or more couplers. Couplers (also known as color modifiers or secondary intermediates) are generally colorless molecules that can form colors in the presence of activated precursors, and are used with other precursors or couplers to generate specific color effects or to stabilize the color.

The choice of precursors and couplers will be determined by the color, shade and intensity of coloration that is desired. The precursors and couplers can be used herein, singly or in combination, to provide dyes having a variety of shades ranging from ash blonde to black.

These compounds are well known in the art, and include aromatic diamines, aromatic diols, aminophenols, and their derivatives (a representative but not exhaustive list of oxidation dye precursor can be found in Sagarin, "Cosmetic Science and Technology", "Interscience, Special Edn. Vol. 2 pages 308 to 310). It is to be understood that the precursors detailed below are only by way of example and are not intended to limit the compositions and processes herein and include the acid addition salts thereof.

Suitable couplers for use in the compositions described herein include, but are not limited to: phenols, resorcinol and naphthol derivatives such as: naphthalene-1,7-diol, benzene-1,3-diol, 4-chlorobenzene-1,3-diol, naphthalen-1-ol, 2-methyl-naphthalen-1-ol, naphthalene-1,5-diol, naphthalene-2,7-diol, benzene-1,4-diol, 2-methyl-benzene-1,3-diol, 7-amino-4-hydroxy-naphthalene-2-sulfonic acid, 2-isopropyl-5-methylphenol, 1,2,3,4-tetrahydro-naphthalene-1,5-diol, 2-chloro-benzene-1,3-diol, 4-hydroxy-naphthalene-1-sulfonic acid, benzene-1,2,3-triol, naphthalene-2,3-diol, 5-dichloro-2-methylbenzene-1,3-diol, 4,6-dichlorobenzene-1,3-diol, 2,3-dihydroxy-[1,4]naphthoquinone; and 1-Acetoxy-2-methylnaphthalene; m-phenylenediamines such as: 2,4-diaminophenol, benzene-1,3-diamine, 2-(2,4-diamino-phenoxy)-ethanol, 2-[(3-amino-phenyl)-(2-hydroxy-ethyl)-amino]-ethanol, 2-methyl-benzene-1,3-diamine, 2-[[2-(2,4-diamino-phenoxy)-ethyl]-(2-hydroxy-ethyl)-amino]-ethanol, 4-{3-[(2,4-diaminophenyl)oxy]-propoxy}benzene-1,3-diamine, 2-(2,4-diamino-phenyl)-ethanol, 2-(3-amino-4-methoxy-phenylamino)-ethanol, 4-(2-amino-ethoxy)-benzene-1,3-diamine, (2,4-diamino-phenoxy)-acetic acid, 2-[2,4-diamino-5-(2-hydroxy-ethoxy)-phenoxy]-ethanol, 4-ethoxy-6-methyl-benzene-1,3-diamine, 2-(2,4-diamino-5-methyl-phenoxy)-ethanol, 4,6-dimethoxy-benzene-1,3-diamine, 2-[3-(2-hydroxy-ethylamino)-2-methyl-phenylamino]-ethanol, 3-(2,4-diamino-phenoxy)-propan-1-ol, N-[3-(dimethylamino)phenyl]urea, 4-methoxy-6-methyl-benzene-1,3-diamine, 4-fluoro-6-methylbenzene-1,3-diamine, 2-({3-[(2-hydroxyethyl)amino]-4,6-dimethoxyphenyl}-amino)ethanol, 3-(2,4-diaminophenoxy)-propane-1,2-diol, 2-[2-amino-4-(methylamino)-phenoxy]ethanol, 2-[(5-amino-2-ethoxy-phenyl)-(2-hydroxy-ethyl)-amino]-ethanol, 2-[(3-aminophenyl)amino]ethanol, 2,4-Diamino-5-(2'-hydroxyethyloxy)toluene; N,N-Dimethyl-3-ureidoaniline; N-(2-aminoethyl)benzene-1,3-diamine, 4-{[(2,4-diamino-phenyl)oxy]methoxy}-benzene-1,3-diamine, 1-methyl-2,6-bis(2-hydroxyethylamino)benzene; and 2,4-dimethoxy-benzene-1,3-diamine; m-aminophenols such as: 3-amino-phenol, 2-(3-hydroxy-4-methyl-phenylamino)-acetamide, 2-(3-hydroxy-phenylamino)-acetamide, 5-amino-2-methyl-phenol, 5-(2-hydroxyethylamino)-2-methyl-phenol, 5-amino-2,4-dichloro-phenol, 3-amino-2-methyl-phenol, 3-amino-2-chloro-6-methyl-phenol, 5-amino-2-(2-hydroxy-ethoxy)-phenol, 2-chloro-5-(2,2,2-trifluoro-ethylamino)-phenol, 5-amino-4-chloro-2-methyl-phenol, 3-cyclopentylamino-phenol, 5-[(2-hydroxyethyl)amino]-4-methoxy-2-methylphenol, 5-amino-4-methoxy-2-methylphenol, 3-(dimethylamino)phenol, 3-(diethylamino)phenol, 5-amino-4-fluoro-2-methylphenol, 5-amino-4-ethoxy-2-methylphenol, 3-amino-2,4-dichloro-phenol, 3-[(2-methoxy-ethyl)amino]phenol, 3-[(2-hydroxyethyl)amino]phenol, 5-amino-2-ethyl-phenol, 5-amino-2-methoxyphenol, 5-[(3-hydroxy-propyl)amino]-2-methylphenol, 3-[(3-hydroxy-2-methylphenyl)-amino]propane-1,2-diol, 3-[(2-hydroxy-ethyl)amino]-2-methyl phenol; 1-Methyl-2-hydroxy-4-(2'-hydroxyethyl)amino-benzene; 1,3-Bis-(2,4-Diaminophenoxy)propane; 1-Hydroxy-2-methyl-5-amino-6-chlorobenzene; and heterocyclic derivatives such as: 3,4-dihydro-2H-1,4-benzoxazin-6-ol, 4-methyl-2-phenyl-2,4-dihydro-3H-pyrazol-3-one, 6-methoxyquinolin-8-amine, 4-methylpyridine-2,6-diol, 2,3-dihydro-1,4-benzodioxin-5-ol, 1,3-benzodioxol-5-ol, 2-(1,3-benzodioxol-5-ylamino) ethanol, 3,4-dimethylpyridine-2,6-diol, 5-chloropyridine-2,3-diol, 2,6-dimethoxypyridine-3,5-diamine, 1,3-benzodioxol-5-amine, 2-{[3,5-diamino-6-(2-hydroxyethoxy)-pyridin-2-yl]oxy}-ethanol, 1H-indol-4-ol, 5-amino-2,6-dimethoxypyridin-3-ol, 1H-indole-5,6-diol, 1H-indol-7-ol, 1H-indol-5-ol, 1H-indol-6-ol, 6-bromo-1,3-benzodioxol-5-ol, 5-aminopyridin-3-ol, pyridine-2,6-diamine, 3-[(3,5-diaminopyridin-2-yl)oxy]propane-1,2-diol, 5-[(3,5-diaminopyridin-2-yl)oxy]pentane-1,3-diol, 1H-indole-2,3-dione, indoline-5,6-diol, 3,5-dimethoxypyridine-2,6-diamine, 6-methoxypyridine-2,3-diamine; 3,4-dihydro-2H-1,4-benzoxazin-6-amine; 4-hydroxy-N-methylindole, 1H-5-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole, 6-methylpyrazolo-[1,5-a]benzimidazole, 2,6-dihydroxypyridine, 2,6-dihydroxy-3,4-dimethylpyridine, 5-methylpyrazolo[5,1-e]-1,2,3-triazole, 5-methyl-6-chloropyrazolo[5,1-e]-1,2,3,-triazole, 5-phenylpyrazolo[5,1-e]-1,2,3-triazole and its addition salts, 1H-2,6-dimethylpyrazolo[1,5-b]-1,2,4-triazole tosylate, 7,8-dicyano-4-methylimidazolo-[3,2-a]imidazole, 2,7-dimethylpyrazolo[1,5-a]pyrimidin-5-one, 2,5-dimethylpyrazolo[1,5-a]pyrimidin-7-one, and 2-methyl-5-methoxymethyl-pyrazolo[1,5-a]pyrimidin-7-one; 6-Hydroxybenzomorpholine; and 3-Amino-2-methylamino-6-methoxypyridine; 1-Phenyl-3-methyl-5-pyrazolone-2,4-dihydro-5,2-phenyl-3H-pyrazole-3-one.

Preferred coupler substances include: N-(3-dimethylaminophenyl)urea, 2,6-diaminopyridine, 2-amino-4-[(2-hydroxyethyl)amino]anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di-[(2-hydroxyethyl)amino]-1,5-dimethoxybenzene, 2,3-diamino-6-methoxypyridine, 3-amino-6-methoxy-2-(methylamino)-pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 2,4-diamino-1-(3-hydroxypropoxy)benzene, 1-(2-aminoethoxy)-2,4-diaminobenzene, 2-amino-1-(2-hydroxyethoxy)-4-methylaminobenzene, 2,4-diaminophenoxyacetic acid, 3-[di(2-hydroxyethyl)-amino]aniline, 4-amino-2-di[(2-hydroxyethyl)amino]-1-ethoxybenzene, 5-methyl-2-(1-methylethyl)phenol, 3-[(2-hydroxyethyl)amino]aniline, 3-[(2-aminoethyl)amino]aniline, 1,3-di(2,4-diaminophenoxy)propane, di-(2,4-diaminophenoxy)methane, 1,3-diamino-2,4-dimethoxybenzene, 2,6-bis-(2-hydroxyethyl)aminotoluene, 4-hydroxyindol, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methyl-phenol, 3-amino-phenol, 2-[(3-hydroxyphenyl)amino]acetamide, 5-[(2-hydroxyethyl)amino]-2-methylphenol, 3-[(2-hydroxyethyl)amino]-phenol, 3-[(2-methoxy-ethyl)amino]-phenol, 5-amino-2-ethylphenol, 2-(4-amino-2-hydroxyphenoxy)-ethanol, 5-[(3-hydroxypropyl)amino]-2-methylphenol, 3-[(2,3-dihydroxypropyl)-amino]-2-methyl-phenol, 3-[(2-hydroxyethyl)amino]-2-methylphenol, 2-amino-3-hydroxypyridine, 5-amino-4-chloro-2-methylphenol, 1-naphthol, 1,5-dihydroxy-naphthalene, 1,7-dihydroxy-naphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hydroxyethyl)amino]-1,3-benzodioxole, 6-bromo-1-hydroxy-3,4-methylenedioxybenzene, 3,4-diaminobenzoic acid, 3,4-dihydro-6-hydroxy-1,4(2H)-benzoxazine, 6-amino-3,4-dihydro-1,4(2H)-benzoxazine, 3-methyl-1-phenyl-5-pyrazolone, 5,6-dihydroxyindole, 5,6- dihydroxyindoline, 5-hydroxy-indole, 6-hydroxyindole, 7-hydroxy-indole and 2,3-indolindione, or their salts.

To produce natural shades and fashionable red tones it is advantageous to use additional primary intermediates (developer substances), such as p-phenylenediamine derivatives, e.g. benzene-1,4-diamine (commonly known as p-phenylenediamine), 2-methyl-benzene-1,4-diamine, 2-chlorobenzene-1,4-diamine, N-phenyl-benzene-1,4-diamine, N-(2-ethoxyethyl)benzene-1,4-diamine, 2-[(4-amino-phenyl)-(2-hydroxy-ethyl)-amino]-ethanol, (commonly known as N,N-bis(2-hydroxyethyl)-p-phenylenediamine) (2,5-diamino-phenyl)-methanol, 1-(2'-Hydroxyethyl)-2,5-diaminobenzene, 2-(2,5-diamino-phenyl)-ethanol, N-(4-aminophenyl)benzene-1,4-diamine, 2,6-dimethyl-benzene-1,4-diamine, 2-isopropyl-benzene-1,4-diamine, 1-[(4-aminophenyl)amino]-propan-2-ol, 2-propyl-benzene-1,4-diamine, 1,3-bis[(4-aminophenyl)(2-hydroxyethyl)amino] propan-2-ol, $N^4,N^4$,2-trimethylbenzene-1,4-diamine, 2-methoxy-benzene-1,4-diamine, 1-(2,5-diaminophenyl) ethane-1,2-diol, 2,3-dimethyl-benzene-1,4-diamine, N-(4-amino-3-hydroxy-phenyl)-acetamide, 2,6-diethylbenzene-1, 4-diamine, 2,5-dimethylbenzene-1,4-diamine, 2-thien-2-ylbenzene-1,4-diamine, 2-thien-3-ylbenzene-1,4-diamine, 2-pyridin-3-ylbenzene-1,4-diamine, 1,1'-biphenyl-2,5-diamine, 2-(methoxymethyl)-benzene-1,4-diamine, 2-(aminomethyl)benzene-1,4-diamine, 2-(2,5-diaminophenoxy) ethanol, N-[2-(2,5-diaminophenoxy)ethyl]-acetamide, N,N-dimethylbenzene-1,4-diamine, N,N-diethylbenzene-1,4-diamine, N,N-dipropylbenzene-1,4-diamine, 2-[(4-aminophenyl)-(ethyl)amino]ethanol, 2-[(4-amino-3-methyl-phenyl)-(2-hydroxy-ethyl)-amino]-ethanol, N-(2-methoxyethyl)-benzene-1,4-diamine, 3-[(4-aminophenyl) amino]propan-1-ol, 3-[(4-aminophenyl)-amino]propane-1, 2-diol, N-{4-[(4-aminophenyl)amino]butyl}benzene-1,4-diamine, and 2-[2-(2-{5-[(2,5-diaminophenyl)-oxy] ethoxy}ethoxy)ethoxy]benzene-1,4-diamine; 1,3-Bis(N(2-Hydroxyethyl)-N-(4-amino-phenyl)amino)-2-propanol; 2,2'-[1,2-Ethanediyl-bis-(oxy-2,1-ethanediyloxy)]-bis-benzene-1,4-diamine; N,N-Bis(2-hydroxyethyl)-p-phenylenediamine; p-aminophenol derivatives such as: 4-amino-phenol (commonly known as p-aminophenol), 4-methylamino-phenol, 4-amino-3-methyl-phenol, 4-amino-2-hydroxymethyl-phenol, 4-amino-2-methyl-phenol, 4-amino-1-hydroxy-2-(2'-hydroxyethylaminomethyl)benzene, 4-amino-methoxymethyl-phenol, 5-amino-2-hydroxy-benzoic acid, 1-(5-amino-2-hydroxy-phenyl)-ethane-1,2-diol, 4-amino-2-(2-hydroxy-ethyl)-phenol, 4-amino-3-(hydroxymethyl)-phenol, 4-amino-3-fluoro-phenol, 4-amino-2-(aminomethyl)-phenol, 4-amino-2-fluoro-phenol; 1-Hydroxy-2,4-diaminobenzene; 1-(2'-Hydroxyethyloxy)-2,4-diaminobenzene; 2,4-Diamino-5-methylphenetol; o-phenylenediamine derivatives such as: 3,4-Diaminobenzoic acid and salts thereof; o-aminophenol derivatives such as: 2-amino-phenol (commonly known as o-aminophenol), 2,4-diaminophenol, 2-amino-5-methyl-phenol, 2-amino-5-ethyl-phenol, 2-amino-6-methyl-phenol, N-(4-amino-3-hydroxy-phenyl)-acetamide, and 2-amino-4-methyl-phenol; and heterocyclic derivatives such as: pyrimidine-2,4,5,6-tetramine (commonly known as 2,4,5,6-tetramino-pyridine), 1-methyl-1H-pyrazole-4,5-diamine, 2-(4,5-diamino-1H-pyrazol-1-yl)ethanol, $N^2,N^2$-dimethyl-pyridine-2,5-diamine, 2-[(3-amino-6-methoxypyridin-2-yl)amino]ethanol, 6-methoxy-$N^2$-methyl-pyridine-2,3-diamine, 2,5,6-triaminopyrimidin-4(1H)-one, pyridine-2,5-diamine, 1-isopropyl-1H-pyrazole-4,5-diamine, 1-(4-methylbenzyl)-1H-pyrazole-4,5-diamine, 1-(benzyl)-1H-pyrazole-4,5-diamine, 1-(4-chlorobenzyl)-1H-pyrazole-4,5-diamine, pyrazolo[1,5-a]-pyrimidine-3,7-diamine, 5,6,7-trimethylpyrazolo[1,5-a] pyrimidin-3-ylamine hydrochloride, 7-methylpyrazolo[1,5-a]pyrimidin-3-ylamine hydrochloride, 2,5,6,7-teramethyl-pyrazolo[1,5-a]pyrimidin-3-ylamine hydrochloride, 5,7-di-tert-butylpyrazolo[1,5-a]pyrimidin-3-ylamine hydrochloride, 5,7-di-trifluoromethyl-pyrazolo[1,5-a]pyrimidin-3-ylamine hydrochloride, 2-methylpyrazolo[1,5-a]pyrimidin-3,7-diamine hydrochloride; 4-hydroxy-2,5,6-triaminopyrimidine; 1-(2'hydroxyethyl)-amino-3,4-methylene dioxybenzene; and 1-hydroxyethyl-4,5-diaminopyrazole sulphate.

Additional primary intermediates (developers) include: N-(3-furylmethyl)benzene-1,4-diamine; N-Thiophen-3-ylmethyl-benzene-1,4-diamine; N-(2-furylmethyl)benzene-1, 4-diamine; N-Thiophen-2-ylmethyl-benzene-1,4-diamine; 4-Hydroxy-benzoic acid (2,5-diamino-benzylidene)-hydrazide; 3-(2,5-Diamino-phenyl)-N-ethyl-acrylamide; 2-[3-(3-Amino-phenylamino)-propenyl]-benzene-1,4-diamine; 2-[3-(4-Amino-phenylamino)-propenyl]-benzene-1,4-diamine; 2-(6-Methyl-pyridin-2-yl)-benzene-1,4-diamine; 2-Pyridin-2-yl-benzene-1,4-diamine; 2-[3-(4-Amino-phenylamino)-propenyl]-benzene-1,4-diamine; 2-[3-(3-Amino-phenylamino)-propenyl]-benzene-1,4-diamine; 3-(2,5-Diamino-phenyl)-N-ethyl-acrylamide; 2-Thiazol-2-yl-benzene-1,4-diamine; 4-Hydroxy-benzoic acid (2,5-diamino-benzylidene)-hydrazide; 3'-Fluoro-biphenyl-2,5-diamine; 2-Propenyl-benzene-1,4-diamine; 2'-Chloro-biphenyl-2,5-diamine; N-Thiophen-3-ylmethyl-benzene-1, 4-diamine; N-(3-furylmethyl)benzene-1,4-diamine; 4'-Methoxy-biphenyl-2,5-diamine; N-(4-Amino-benzyl)-benzene-1,4-diamine; 2-Methyl-5-[(1-H-pyrrol-2-ylmethyl)-amino]-phenol; 5-[(Furan-2-ylmethyl)-amino]-2-methyl-phenol; 5-Isopropylamino-2-methyl-phenol; Biphenyl-2,4,4'-triamine hydrochloride; 5-(4-Amino-phenyl) aminomethyl-benzene-1,3-diamine hydrochloride; 5-Phenylaminomethyl-benzene-1,3-diamine hydrochloride; 2-[4-Amino-2-(3,5-diamino-benzylamino)-phenoxy]-ethanol hydrochloride; 5-(3-Amino-phenyl)aminomethyl-benzene-1,3-diamine hydrochloride; N-(2-Amino-benzyl)-benzene-1,3-diamine hydrochloride; N-Furan-2-ylmethyl-benzene-1,3-diamine hydrochloride; 2-[(3-Amino-phenylamino)-methyl]-phenol hydrochloride; 4-Amino-2-propylaminomethyl-phenol; hydrochloride; N-Benzo[1,3] dioxol-5-ylmethyl-benzene-1,3-diamine hydrochloride; N-[4-Amino-2-(2-hydroxyethyl)-2H-pyrazol-3-yl]-3-(5-amino-2-hydroxy-phenyl)-acrylamide; hydrochloride; 4-Amino-2-(isopropylamino-methyl)-phenol; hydrochloride; 4-Thiophen-3-yl-benzene-1,3-diamine; hydrochloride; 5-Phenylaminomethyl-benzene-1,3-diamine hydrochloride; 5-(3-Amino-phenyl)aminomethyl-benzene-1,3-diamine hydrochloride; 4-Thiophen-3-yl-benzene-1,3-diamine; hydrochloride; 2',4'-Diamino-biphenyl-4-ol; hydrochloride; 5-Cyclobutylamino-2-methyl-phenol; 5-Cyclobutylamino-2-methyl-phenol; 4-Amino-2-(pyridin-3-ylaminomethyl)-phenol; 5-(3-Amino-phenyl)aminomethyl-benzene-1,3-diamine hydrochloride; 5-Allylaminomethyl-benzene-1,3-diamine hydrochloride; N-(4-Amino-benzyl)-benzene-1,3-diamine hydrochloride; N-Benzyl-benzene-1,3-diamine hydrochloride; 3-[(3-Amino-phenylamino)-methyl]-phenol hydrochloride; N-(4-Methoxy-benzyl)-benzene-1,3-diamine hydrochloride; N-Thiophen-2-ylmethyl-benzene-1,3-diamine hydrochloride; 4-Amino-2-[(2-hydroxy-5-nitro-phenylamino)-methyl]-phenol; hydrochloride; 2',4'-Diamino-biphenyl-4-ol hydrochloride; Biphenyl-2,4,4'-triamine; 5-(4-Amino-phenyl)aminomethyl-benzene-1,3-diamine hydrochloride; 2-[4-Amino-2-(3,5-diamino-benzylamino)-phenoxy]-ethanol hydrochloride; 5-Allylaminomethyl-benzene-1,3-diamine hydrochloride; 5-(3-Amino-phenyl)aminomethyl-benzene-1,3-diamine hydrochloride; N-(4-Amino-benzyl)-benzene-1,3-diamine hydrochloride; N-Benzyl-benzene-1,3-diamine hydrochloride; 3-[(3-Amino-phenylamino)-methyl]-phenol hydrochloride; N-(2-Amino-benzyl)-benzene-1,3-diamine hydrochloride; N-(4-Methoxy-benzyl)-benzene-1,3-diamine hydrochloride; N-Furan-2-ylmethyl-benzene-1,3-diamine hydrochloride; 2-[(3-Amino-phenylamino)-methyl]-phenol hydrochloride; N-Thiophen-2-ylmethyl-benzene-1,3-diamine hydrochloride; N-Benzol[1,3]dioxol-5-ylmethyl-benzene-1,3-diamine hydrochloride; N-[4-Amino-2-(2-hydroxy-ethyl)-2H-pyrazol-3-yl]-3-(5-amino-2-hydroxy-phenyl)-acrylamide hydrochloride; 4-Amino-2-propylaminomethyl-phenol; hydrochloride; 4-Amino-2-(isopropylamino-methyl)-phenol hydrochloride; 4-Amino-2-[(2-hydroxy-5-nitro-phenylamino)-methyl]-phenol hydrochloride; 2-Methyl-5-[(1-H-pyrrol-2-ylmethyl)-amino]-phenol; 5-[(Furan-2-ylmethyl)-amino]-2-methyl-phenol; 5-Isopropylamino-2-methyl-phenol; 5-Cyclobutylamino-2-methyl-phenol; 4-Amino-2-(pyridin-3-ylaminomethyl)-phenol; and 5-Cyclobutylamino-2-methylphenol.

The following compounds are especially suitable as primary intermediates (developer compounds): 1,4-diamino-2,6-dimethylbenzene, 1,4-diamino-2,5-dimethylbenzene, 1,4-diamino-2,3-dimethylbenzene, 2-chloro-1,4-diaminobenzene, 4-phenylaminoaniline, 4-dimethylaminoaniline, 4-diethylamino-aniline, 4-[di(2-hydroxyethyl)amino]aniline, 4-[(2-methoxyethyl)amino]-aniline, 4-[(3-hydroxypropyl)amino]aniline, 1,4-diamino-2-(2-hydroxyethyl)benzene, 1,4-diamino-2-(1-methylethyl)benzene, 1,3-bis-[(4-aminophenyl)-(2-hydroxyethyl)amino]-2-propanol, 1,8-bis-(2,5-diaminophenoxy)-3,6-dioxaoctane, 4-aminophenol, 4-amino-3-methylphenol, 4-methyl-aminophenol, 4-amino-2-(aminomethyl)phenol, 4-amino-2-[(2-hydroxyethyl)amino]-methylphenol, 4-amino-2-(methoxymethyl)phenol, 4-amino-2-(2-hydroxyethyl)phenol, 5-amino-salicylic acid, 2,5-diaminopyridine, 2,4,5,6-tetramino-pyrimidine, 2,5,6-triamino-4-(1H)-pyrimidone, 4,5-diamino-1-(2-hydroxyethyl)-1H-pyrazole, 4,5-diamino-1-(1-methylethyl)-1H-pyrazole, 4,5-diamino-1-[(4-methylphenyl)-methyl]-1H-pyrazole, 1-[(4-chlorophenyl)methyl]-4,5-diamino-1H-pyrazole, 4,5-diamino-1-methyl-1H-pyrazole, 4,5-diamino-3-methyl-1-phenyl-1H-pyrazole, 4,5-diamino-1-(2-hydroxyethyl)-3-methyl-1H-pyrazole, 2-amino-phenol, 2-amino-6-methylphenol, 2-amino-5-ethyl-phenol, 2-methoxymethyl, 1-4-diaminobenzene and 2-amino-5-methyl-phenol, or their salts.

The hair colouring compositions of the present invention may also include non oxidative hair dyes. i.e. direct dyes which may be used alone or in combination with the above described oxidative dyes. Suitable direct dyes include direct-dyeing anionic, cationic or non-ionic dye compounds, such as azo or anthraquinone dyes and nitro derivatives of the benzene series and mixtures thereof. Such direct dyes are particularly useful to deliver shade modification or highlights.

The following are preferred examples of anionic direct-dyeing dye compounds for use in the compositions of the invention: 6-hydroxy-5-[(4-sulfophenyl)azo]-2-naphthalene sulfonic acid disodium salt (C.I. 15985; Food Yellow No. 3; FD&C Yellow No. 6), 2,4-dinitro-1-naphthol-7-sulfonic acid disodium salt (C.I.10316; Acid Yellow No. 1; Food Yellow No. 1), 2-(indan-1,3-dion-2-yl)quinoline-x,x-sulfonic acid (mixture of mono- and disolfuonic acid) (C.I.47005; D&C Yellow No. 10; Food Yellow No. 13, Acid Yellow No. 3), 5-hydroxy-1-(4-sulfophenyl)-4-[(4-sulfophenyl)azo]pyrazole-3-carboxylic acid sodium salt (C.I. 19140; Food Yellow No. 4; Acid Yellow No. 23), 9-(2-carboxyphenyl)-6-hydroxy-3H-xanthen-3-one (C.I.45350; Acid Yellow No. 73; D&C Yellow No. 8), 5-[(2,4-dinitrophenyl)amino]-2-phenylaminobenzenesulfonic acid sodium salt (C.I.10385; Acid Orange No. 3), 4-[(2,4-dihydroxyphenyl)azo]-benzene sulfonic acid monosodium salt (C.I.14270; Acid Orange No. 6), 4-[(2-hydroxynaphth-1-yl)azo]benzenesulfonic acid sodium salt (C.I. 15510; Acid Orange No. 7), 4-[(2,4-dihydroxy-3-[(2,4-dimethylphenyl)azo]phenyl)azo]-benzene sulfonic acid sodium salt (C.I.20170; Acid Orange No. 24), 4-hydroxy-3-[(4-sulfonaphth-1-yl)azo]-1-naphthalene sulfonic acid disodium salt (C.I. 14720; Acid Red No. 14), 6-hydroxy-5-[(4-sulfonaphth-1-yl)azo]-2,4-naphthalene-disulfonic acid trisodium salt (C.I. 16255; Ponceau 4R; Acid Red No. 18), 3-hydroxy-4-[(4-sulfonaphth-1-yl)azo]-2,7-naphthalene-disulfonic acid trisodium salt (C.I. 16185; Acid Red No. 27), 8-amino-1-hydroxy-2-(phenylazo)-3,6-naphthalene disulfonic acid disodium salt (C.I.17200; Acid Red No. 33), 5-(acetylamino)-4-hydroxy-3-[(2-methylphenyl)azo]-2,7-naphthalene disulfonic acid disodium salt (C.I.18065; Acid Red No. 35), 2-(3-hydroxy-2,4,5,7-tetraiodo-dibenzopyran-6-on-9-yl)-benzene sulfonic acid disodium salt (C.I. 45430; Acid Red No. 51), N-[6-(diethylamino)-9-(2,4-disulfophenyl)-3H-xanthen-3-yliden]-N-ethylethanaminium hydroxide, inner Salt, sodium salt (C.I.45100; Acid Red No. 52), 8-[(4-(phenylazo)phenyl)azo]-7-naphthol-1,3-disulfonic acid disodium salt (C.I. 27290; Acid Red No. 73), 2',4',5',7'-tetrabromo-3',6'-dihydroxyspiro[isobenzofuran-1-(3H),9'-[9H]xanthen]-3-one disodium salt (C.I.45380; Acid Red No. 87), 2',4',5',7'-tetrabromo-4,5,6,7-tetrachloro-3',6'-dihydroxyspiro[isobenzofuran-1 (3H),9'[9H]xanthen]-3-one disodium salt (C.I. 45410; Acid Red No. 92), 3',6'-dihydroxy-4',5'-diiodospiro[isobenzofuran-1 (3H),9'[9H]xanthen)-3-one disodium salt (C.I. 45425; Acid Red No. 95), (2-sulfophenyl)-di-4-(ethyl-((4-sulfophenyl)methyl)-amino)phenyl]carbenium disodium salt, betaine (C.I. 42090; Acid Blue No. 9; FD&C Blue No. 1), 1,4-bis-[(2-sulfo-4-methylphenyl)amino]-9,10-anthraquinone disodium salt (C.I. 61570; Acid Green No. 25), bis-[4-(dimethylamino)phenyl]-(3,7-disulfo-2-hydroxynaphth-1-yl)carbenium inner salt, monosodium salt (C.I. 44090; Food Green No. 4; Acid Green No. 50), bis-[4-(diethylamino)phenyl](2,4-disulfophenyl)carbenium inner salt, sodium salt (2:1) (C.I. 42045; Food Blue No. 3; Acid Blue No. 1), bis[4-(diethylamino)phenyl]-(5-hydroxy-2,4-disulfophenyl)carbenium inner salt, calcium salt (2:1) (C.I. 42051; Acid Blue No. 3), 1-amino-4-(cyclohexylamino)-9,10-anthraquinone-2-sulfonic acid sodium salt (C.I. 62045; Acid Blue No. 62), 2-(1,3-dihydro-3-oxo-5-sulfo-2H-indol-2-yliden)-2,3-dihydro-3-oxo-1H-indol-5-sulfonic acid disodium salt (C.I. 73015; Acid Blue No. 74), 9-(2-carboxyphenyl)-3-[(2-methylphenyl)-amino]6-[(2-methyl-4-sulfophenyl)amino]xanthylium inner salt, monosodium salt (C.I. 45190; Acid Violet No. 9), 1-hydroxy-4-[(4-methyl-2-sulfophenyl)amino]-9,10-anthraquinone sodium salt (C.I. 60730; D&C Violet No. 2; Acid Violet No. 43), bis-[3-nitro-4-[(4-phenylamino)-3-sulfophenylamino]phenyl]-sulfone (C.I. 10410; Acid Brown No. 13), 5-amino-4-hydroxy-6-[(4-nitrophenyl)azo]3-(phenylazo)-2,7-naphthalene disulfonic acid disodium salt (C.I.20470; Acid Black No. 1), 3-hydroxy-4-[(2-hydroxynaphth-1-yl)azo]-7-nitronaphthalenesulfonic acid chromium complex (3:2) (C.I. 15711; Acid Black No. 52), 3-[(2,4-dimethyl-5-sulfophenyl)azo]-4-hydroxy-1-naphthalene-sulfonic acid disodium salt (C.I. 14700; Food Red No. 1; Ponceau SX; FD&C Red No. 4), 4-(acetylamino)-5-hydroxy-6-[(7-sulfo-4-[(4-sulfophenyl)azo]naphth-1yl)azo]-1,7-naphthalene disulfonic acid tetrasodium salt (C.I. 28440; Food Black No. 1), 3-hydroxy-4-(3- methyl-5-oxo-1-phenyl-4,5-dihydro-1H-pyrazole-4-yl-azo)-naphthalene-1-sulfonic acid sodium salt chromium complex (Acid Red No. 195).

The following are preferred cationic direct-dyeing dye compounds: 9-(dimethylamino)-benzo[a]phenoxazin-7-ium chloride (C.I. 51175; Basic Blue No. 6), di[4-(diethylamino)phenyl]-[4-(ethylamino)naphthyl]carbenium chloride (C.I. 42595; Basic Blue No. 7), 3,7-di(dimethylamino)phenothiazin-5-ium chloride (C.I. 52015; Basic Blue No. 9), di[4-dimethylamino)phenyl][4(phenylamino)naphthyl]carbenium chloride (C.I. 44045; Basic Blue No. 26), 2-[(4-(ethyl (2-hydroxyethyl)amino)phenyl)azo]-6-methoxy-3-methylbenzothiazol ium methylsulfate (C.I. 11154; Basic Blue No. 41), 8-amino-2-bromo-5-hydroxy-4-imino-6-[(3-(trimethylammonio)phenyl)amino]-1 (4H)naphthalenone chloride (C.I.56059; Basic Blue No. 99), bis-[4-(dimethylamino)phenyl][4-(methylamino)phenyl]carbenium chloride (C.I. 42535; Basic Violet No. 1) tris-(4-amino-3-methylphenyl)carbenium chloride (C.I. 425 20; Basic Violet No. 2), tris-[4-(dimethylamino)phenyl]carbenium chloride (C.I. 42555; Basic Violet No. 3), 2-[3,6-(diethylamino)dibenzopyranium-9-yl]benzoic acid chloride (C.I. 45170; Basic Violet No. 10), di(4-aminophenyl)(4-amino-3-methylphenyl)carbenium chloride (C.I. 42510; Basic Violet No. 14), 1,3-bis[(2,4-diamino-5-methylphenyl)azo]-3-methylbenzene (C.I. 21010; Basic Brown No. 4), 1-[(4-aminophenyl)azo]-7-(trimethylammonio)-2-naphthol chloride (C.I. 12250; Basic Brown No. 16), 1-[(4-amino-2-nitrophenyl)azo]-7-(trimethylammonio)-2-naphthol chloride (C.I. 12251; Basic Brown No. 17), 1-[(4-amino-3-nitrophenyl)azo]-7-(trimethylammonio)-2-naphthol chloride (C.I. 12251; Basic Brown No. 17), 3,7-diamino-2,8-dimethyl-5-phenylphenazinium chloride (C.I. 50240; Basic Red No. 2), 1,4-dimethyl-5-[(4(dimethylamino)phenyl)azo]-1,2,4-triazolium chloride (C.I. 11055; Basic Red No. 22), 2-hydroxy-1-[(2-methoxyphenyl)azo]-7-(trimethylammonio)naphthalene chloride (C.I. 12245; Basic Red No. 76), 2-[2-((2,4-dimethoxyphenyl)amino)ethenyl]-1,3,3-trimethyl-3H-indol-1-ium-chloride (C.I. 48055; Basic Yellow No. 11), 3-methyl-1-phenyl-4-[(3-(trimethylammonio)phenyl)azo]-pyrazole-5-one chloride (C.I. 12719; Basic Yellow No. 57), bis-[4-(diethylamino)phenyl]phenylcarbenium hydrogen sulfate (1:1) (C.I. 42040; Basic Green No. 1).

To improve the color balance and to produce special shades the following nonionic direct-dyeing dye compounds have proven to be useful in the compositions according to the invention:

1-amino-2-[(2-hydroxyethyl)amino]-5-nitrobenzene (HC Yellow No. 5), 1-(2-hydroxyethoxy)-2-[(2-hydroxyethyl)amino]-5-nitrobenzene (HC Yellow No. 4), 1-[(2-hydroxyethyl)amino]-2-nitrobenzene (HC Yellow No. 2), 2-[(2-hydroxyethyl)amino]-1-methoxy-5-nitrobenzene, 2-amino-3-nitrophenol, 1-(2-hydroxyethoxy)-3-methylamino-4-nitrobenzene, 2,3-(dihydroxy-propoxy)-3-methylamino-4-nitrobenzene, 2-[(2-hydroxyethyl)amino]-5-nitrophenol (HC Yellow No. 11), 3-[(2-aminoethyl)amino]-1-methoxy-4-nitrobenzene hydrochloride (HC Yellow No. 9), 1-[(2-ureidoethyl)amino]-4-nitrobenzene, 4-[(2,3-dihydroxypropyl)amino]-3-nitro-1-trifluoromethylbenzene (HC Yellow No. 6), 1-chloro-2,4-bis-[(2-hydroxyethyl)amino]-5-nitrobenzene (HC Yellow No. 10), 4-[(2-hydroxyethyl)amino]-3-nitro-1-methylbenzene, 1-chloro-4-[(2-hydroxyethyl)amino]-3-nitrobenzene (HC Yellow No. 12), 4-[(2-hydroxyethyl)-amino]-3-nitro-1-trifluoromethylbenzene (HC Yellow No. 13), 4-[(2-hydroxyethyl)amino]-3-nitrobenzonitrile (HC Yellow No. 14), 4-[(2-hydroxyethyl)amino]-3-nitrobenzamide (HC Yellow No. 15), 1-amino-4-[(2-hydroxyethyl)amino]-2-nitrobenzene (HC Red No. 7), 2-amino-4,6-dinitrophenol, 2-ethylamino-4,6-dinitrophenol, 4-amino-2-nitrodiphenylamine (HC Red No. 1), 1-amino-4-[di(2-hydroxyethyl)amino]-2-nitrobenzene hydrochloride (HC Red No. 13), 1-amino-5-chloro-4-[(2hydroxyethyl)amino]-2-nitrobenzene, 4-amino-1-[(2-hydroxyethyl)-amino]-2-nitrobenzene (HC Red No. 3), 4-amino-3-nitrophenol, 4-[(2-hydroxyethyl)amino]-3-nitrophenol, 1-[(2-aminoethyl)amino]4-(2-hydroxyethoxy)-2-nitrobenzene (HC Orange No. 2), 4-(2,3-dihydroxypropoxy)-1-[(2-hydroxyethyl)amino]-2-nitrobenzene (HC Orange No. 3), 1-amino-5-chloro-4-[(2,3-dihydroxypropyl)amino]-2-nitrobenzene (HC Red No. 10), 5-chloro-1,4-[di(2,3-dihydroxypropyl)amino]-2-nitrobenzene (HC Red No. 11), 2-[(2-hydroxyethyl)-amino]-4,6-dinitrophenol, 4-ethylamino-3-nitrobenzoic acid, 2-[(4-amino-2-nitrophenyl)amino]-benzoic acid, 2-chloro-6-methylamino-4-nitrophenol 2-chloro-6-[(2-hydroxyethyl)amino]4-nitrophenol, 2-chloro-6-ethylamino-4-nitrophenol, 2-amino-6-chloro-4-nitrophenol, 4-[(3-hydroxypropyl)-amino]-3-nitrophenol, 2,5-diamino-6-nitropyridine, 1,2,3,4-tetrahydro-6-nitrochinoxalin, 7-amino-3,4-dihydro-6-nitro-2H-1,4-benzoxazine (HC Red No. 14), 1,4-bis-[(2-hydroxyethyl)-amino]-2-nitrobenzene, 1-(2-hydroxyethyl)amino-2-nitro-4-[di(2-hydroxyethyl)amino]benzene (HC Blue No. 2), 1-amino-3-methyl-4-[(2-hydroxyethyl)amino]-6-nitrobenzene (HC Violet No. 1), 4-[ethyl-(2-hydroxyethyl)amino]-1-[(2-hydroxyethyl)amino]-2-nitrobenzene hydrochloride (HC Blue No. 12), 4-[di(2-hydroxyethyl)amino]-1-[(2-methoxyethyl)amino]-2-nitrobenzene (HC Blue No. 11), 1-[(2,3-dihydroxy-propyl)amino]4-[methyl-(2-hydroxyethyl)amino]-2-nitrobenzene (HC Blue No. 10), 1-[(2,3-dihydroxypropyl)amino]4-[ethyl-(2-hydroxyethyl)amino]-2-nitrobenzene hydrochloride (HC Blue No. 9), 1-(3-hydroxypropylamino)-4-[di(2-hydroxyethyl)amino]-2-nitrobenzene (HC Violet No. 2), 1-methylamino-4-[methyl-(2,3-dihydroxypropyl)amino]-2nitrobenzene (HC Blue No. 6), 2-((4-amino-2-nitrophenyl)amino)-5-dimethylaminobenzoic acid (HC Blue No. 13), 1,4-di[(2,3-dihydroxypropyl)amino]-9,10-anthraquinone, 1-[(2-hydroxyethyl)amino]4-methylamino-9,10-anthraquinone (C.I. 61505, disperse Blue No. 3), 2-[(2-aminoethyl)amino]-9,10-anthraquinone (HC Orange No. 5), 1-hydroxy-4-[(4-methyl-2-sulfophenyl)amino]-9,10-anthraquinone, 1-[(3-aminopropyl)amino]4-methylamino-9,10-anthraquinone (HC Blue No. 8), 1-[(3-aminopropyl)amino]-9,10-anthraquinone (HC Red No. 8), 1,4-diamino-2-methoxy-9,10-anthraquinone (C.I.62015, disperse Red No. 11, Solvent Violet No. 26), 1,4-dihydroxy-5,8-bis[(2-hydroxyethyl)amino-9,10-anthraquinone (C.I. 62500, disperse Blue No. 7, Solvent Blue No. 69), 1-[di-(2-hydroxyethyl)amino]-3-methyl-4-[(4-nitrophenyl)azo]benzene (C.I. 11210, disperse Red No. 17), 4-[(4-aminophenyl)azo]-1-[di(2-hydroxyethyl)amino]-3-methylbenzene (HC Yellow No. 7), 2,6-diamino-3-[(pyridine-3-yl)azo]pyridine, 2-((4-(acetylamino)phenyl)-azo)-4-methylphenol (C.I. 11855; disperse Yellow No. 3).

The following compounds may also be used as direct-dyeing dye compounds: 2-amino-4,6-dinitrophenol, 2-ethylamino-4,6-dinitrophenol, 2-[(2-hydroxyethyl)-amino]4,6-dinitrophenol and dye compounds of the following general formula (V):

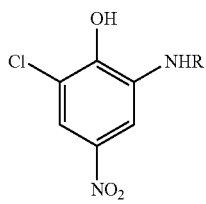

formula (V)

wherein R represents hydrogen, methyl, ethyl or hydroxyethyl.

The hair dye compositions of the present invention will generally comprise from about 0.001% to about 10% by weight of direct dyes, preferably from about 0.1% to about 5% by weight, more preferably from about 0.2% to about 2% by weight.

The present invention may also include fluorescent dyes, i.e. dyes which are molecules that colour by themselves, and thus absorb light in the visible and possibly the ultraviolet spectrum (wavelengths ranging from 360 to 760 nanometers), but which, in contrast with a standard dye, converts the absorbed energy into fluorescent light of longer wavelength emitted in the visible region of the spectrum.

Example fluorescent dyes that may be used include the fluorescent dyes belonging to the following families: naphthalimides; cationic or non-cationic coumarins; xanthenodiquinolizines (such as, especially, sulphorhodamines); azaxanthenes; naphtholactams; azlactones; oxazines; thiazines; dioxazines; polycationic fluorescent dyes of azo, azomethine or methine type, alone or as mixtures, and preferably belonging to the following families: naphthalimides; cationic or non-cationic coumarins; azaxanthenes; naphtholactams; azlactones; oxazines; thiazines; dioxazines; polycationic fluorescent dyes of azo, azomethine or methine type, alone or as mixtures.

The fluorescent dye(s) present in the composition according to the invention advantageously represent(s) from 0.01% to 20% by weight, more particularly from 0.05% to 10% by weight and preferably from 0.1% to 5% by weight, relative to the total weight of the composition.

The hair dye compositions of the present invention will generally comprise from about 0.001% to about 10% of dyes. For example compositions providing low intensity dyeing such as natural blonde to light brown hair shades generally comprise from about 0.001% to about 5%, preferably from about 0.1% to about 2%, more preferably from about 0.2% to about 1% by weight of dyeing composition of precursors and couplers. Darker shades such as browns and black typically comprise from 0.001% to about 10% by weight, preferably from about 0.05% to about 7% by weight, more preferably form about 1% to about 5% of precursors and couplers.

Oxidizing Agent

The compositions according to the present invention comprise an oxidizing agent. Preferred oxidizing agents for use herein are water-soluble peroxygen oxidizing agents. "Water-soluble" as defined herein means that in standard condition at least 0.1 g, preferably 1 g, more preferably 10 g of said oxidizing agent can be dissolved in 1 liter of deionized water. The oxidizing agents are valuable for the initial solubilisation and decolorisation of the melanin (bleaching) and accelerate the oxidation of the oxidative dye precursors (oxidative dyeing) in the hair shaft.

Any oxidizing agent known in the art may be utilized in the present invention. Preferred water-soluble oxidizing agents are inorganic peroxygen materials capable of yielding hydrogen peroxide in an aqueous solution. Water-soluble peroxygen oxidizing agents are well known in the art and include hydrogen peroxide, inorganic alkali metal peroxides such as sodium periodate and sodium peroxide and organic peroxides such as urea peroxide, melamine peroxide, and inorganic perhydrate salt bleaching compounds, such as the alkali metal salts of perborates, percarbonates, perphosphates, persilicates, persulphates and the like. These inorganic perhydrate salts may be incorporated as monohydrates, tetrahydrates etc. Alkyl and aryl peroxides and or peroxidases may also be used. Mixtures of two or more such oxidizing agents can be used if desired. The oxidizing agents may be provided in aqueous solution or as a powder which is dissolved prior to use. Preferred for use in the compositions according to the present invention are hydrogen peroxide, percarbonate (which may be used to provide a source of both oxidizing agent and carbonate ions), persulphates and combinations thereof.

In a preferred embodiment of the present invention the composition comprises peroxymoncarbonate ions, (preferably formed in-situ from hydrogen peroxide and a carbonate ion source) which in combination with an alkalizing agent and the specific dyes defined hereinafter, at a pH of up to and including 9.5 can deliver further improvements of the desired hair colour results, whilst reducing the odour and the damage to the hair fibres.

Whilst not wishing to be bound by theory, it is believed that the peroxymonocarbonate (—OC(O)OOH), ion which is then the key species responsible for the bleaching of the melanin decomposes at pH values above 9.5 to form oxygen and the hydrogen carbonate ion. At pH values below 7.5 the hydrogen carbonate ion decomposes to form carbon dioxide and water. At pH values of 9.0 the bleaching of the melanin and the final colour observed is at an optimal level. Thus surprisingly, this allows for the delivery of improved lift, that is hair lightening which is a highly desirable consumer need. Furthermore, compositions having a pH lower than 9.5 have the benefit that the unpleasant ammonia odour is significantly reduced which allows for the formation of a hair colouring product that delivers the desired lightening and colour with a pleasant cosmetic-like odour. In addition, the peroxymonocarbonate ions at the lower pH of 9.5 causes less fibre damage than current colouring systems. In particular this gives better hair fibre appearance and thus improved hair shine and colour appearance.

According to the present invention the compositions comprise from about 0.1% to about 10% by weight, preferably from about 1% to about 7% by weight, and most preferably from about 2% to about 6% by weight of an oxidizing agent.

Carbonate Ion Source

According to the present invention the compositions may also comprise at least a source of carbonate ions or carbamate ions or hydrocarbonate ions or any mixture thereof. Any source of these ions may be utilized. Suitable sources for use herein include sodium, potassium, guanidine, arginine, lithium, calcium, magnesium, barium, ammonium salts of carbonate, carbamate and hydrocarbonate ions and mixtures thereof such as sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof. Percarbonate salts may also be utilized to provide both the source of carbonate ions and oxidizing agent. Preferred sources of carbonate ions, carbamate ions and hydrogencarbonate ions are sodium hydrogen carbonate, potassium hydrogen carbonate, ammonium carbamate and mixtures thereof.

The compositions of the present invention may comprise from about 0.1% to about 5%, preferably from about 0.11% to about 10% by weight, more preferably from about 1% to about 8% by weight of the carbonate hydrogen carbonate or carbonate ion source ion. Preferably, if present, the ammonium ions and carbonate ions are present in the composition at a weight ratio of from 3:1 to 1:10, preferably 2:1 to 1:5. In a particularly preferred embodiment of the present invention the ammonium ions and carbonate ion sources are provided by a single source such as ammonium carbonate, ammonium hydrogen carbonate, ammonium hydrocarbonate or mixtures thereof.

Alkalizing Agent

According to the present invention the composition may also comprises an alkalizing agent, preferably a source of ammonium ions and or ammonia. Any agent known in the art may be used such as alkanolamides for example monoethanolamine, diethanolamine, triethanolamine, monopropanolamine, dipropanolamine, tripropanolamine, 2-amino-2-methyl-1,3-propanediol, 2-amino-2-methyl-1-propanol, and 2-amino-2-hydroxymethyl-1,3-propanediol and guanidium salts. Particularly, preferred alkalizing agents are those which provide a source of ammonium ions. Any source of ammonium ions is suitable for use herein. Preferred sources include ammonium chloride, ammonium sulphate, ammonium nitrate, ammonium phosphate, ammonium acetate, ammonium carbonate, ammonium hydrogen carbonate, ammonium carbamate, ammonium hydroxide, percarbonate salts, ammonia and mixtures thereof. Particularly preferred are ammonium carbonate, ammonium carbamate, ammonia and mixtures thereof.

The compositions of the present invention may comprise from about 0.1% to about 10% by weight, preferably from about 0.5% to about 5%, most preferably from about 1% to about 3% of an alkalizing agent, preferably ammonium ions.

pH

The compositions of the present invention may have a pH of from 8 to 12, preferably from 8 to 10. For embodiments comprising a peroxymoncarbonate ion the pH is preferably up to and including pH 9.5, more preferably from about 9.5 to about 7.5, even more preferably from about 9.5 to about 8.4 and most preferably from about 9.4 to about 8.5 and even more preferably about pH 9.0.

The pH of the compositions can be determined by using either a Mettler Toledo MP220 or a MP225 pH equipment, fitted with a standard laboratory pH electrode. The equipment is calibrated before each use using standard calibration buffers and using the standard calibration procedure.

It is known that for good lightening and good colour formation that the final formulation should have a good buffering capacity or reserve alkalinity (the ability of the system to resist the pH shift that would otherwise be caused by addition of acid). The reserve alkalinity is measured using a Mettler DL70 auto-titrator with 0.1 N methanolic hydrochloric acid being added to 0.7 mL of thoroughly mixed colourant product in 50 mL of methanol. The electrode is calibrated and then used to measure the amount of acid required to reach the sharpest end point triggered by a rapid change in pH. Using this method it has been determined that a reserve alkalinity of at least 0.2 ml of 0.1N of ethanolic hydrochloric acid and preferably above 0.4 is required for good lightening and colouring. Suitable buffering systems include ammonia/ammonium acetate mixtures, monoethanolamine tetrasodium pyrophosphate, isopropanolamine, benzoic acid.

Radical Scavenger

According to the present invention the compositions may further comprise a source of radical scavenger. As used herein the term radical scavenger refers to a species that can react with a carbonate radical to convert the carbonate radical by a series of fast reactions to a less reactive species, i.e. a carbonate radical scavenger.

Suitable radical scavengers for use herein may be selected from the classes of alkanolamines, amino sugars, amino acids, esters of amino acids and mixtures thereof. Particularly preferred compounds are: monoethanolamine, 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamic acid, tryptophan, and mixtures thereof, and the salts such as the potassium, sodium and ammonium salts thereof and mixtures thereof.

Especially preferred compounds are glycine, sarcosine, lysine, serine, 2 methoxyethylamine, glucosamine, glutamic acid, morpholine, piperidine, ethylamine, 3 amino-1-propanol and mixtures thereof.

The compositions of the present invention preferably comprise from about 0.1% to about 10% by weight, preferably from about 1% to about 7% by weight of radical scavenger. Preferably, the radical scavenger is present at an amount such that the weight ratio of radical scavenger to carbonate ion is from 2:1 to 1:4. The radical scavenger is also preferably selected such that it is not an identical species as the alkalizing agent. According to one embodiment of the present invention the radical scavenger may be formed in situ in the hair dyeing compositions prior to application to the hair fibres.

Surfactants

The compositions according to the present invention may further comprise at least about 0.01% of a surfactant. Surfactants suitable for use herein generally have a lipophilic chain length of from about 8 to about 30 carbon atoms and can be selected from anionic, nonionic, amphoteric and cationic surfactants and mixtures thereof.

Gel Network Thickener

According to the present invention, the hair colouring compositions may comprise a gel network thickener system. The gel network thickener system is defined as a thickening system comprising a ternary surfactant system comprising a) at least one surfactant or amphophile having an HLB of 6 or less and a melting point of at least 30° C., b) at least one surfactant selected from anionic surfactants according to the formula $R_nX_mYM$, wherein R is independently selected from alkyl, alkenyl or alkylaryl groups having from 8 to 30 carbon atoms, X is independently selected from polar groups comprising at least one carbon atom and at least one oxygen or nitrogen atom, Y is an anionic group selected from carboxylates, sulphates, sulphonates or phosphates, n and m are independently 1 or 2 and M is hydrogen or a salt forming cation and mixtures thereof, or cationic surfactants selected from quaternary ammonium salts or amido-amines having at least one fatty chain comprising at least 20 carbon atoms and mixtures thereof and c) at least one non-ionic surfactant having an HLB of 7 or more, and comprising one or more polyethyleneoxide chains.

The HLB (hydrophilic-lipophilic balance) of the surfactant(s) used according to the invention is the standard HLB according to Griffin defined in publication J. Soc. Cosm. Chem., Vol. 5, 1954, p. 249, the disclosure of which is incorporated herein by reference.

The melting point of the surfactant(s) used according to the invention can be measured by a standard melting point method as described in U.S. Pharmacopeia, USP-NF General Chapter <741> "Melting range or temperature".

The gel network system comprises as a first surfactant, a low HLB surfactant or amphophile has an HLB of 6 or less and melting point of at least about 30° C. Representative examples include the following compounds (in the examples below "solid" refers to the material state at temperature below 30° C.): solid fatty alcohols, solid oxyethylenated fatty alcohols, solid glycol esters, solid oxyethylenated alkyl phenols, solid sorbitan esters, solid sugar esters, solid methyl glucoside esters, solid polyglycerine esters, solid alkyl glyceryl ethers, solid propylene glycol fatty acid esters, cholesterol and ceramides.

Preferably, the low HLB surfactants are selected from linear or branched fatty alcohols comprising from about 14 to 30 carbon atoms, oxyethylenated fatty alcohols comprising from about 16 to 30 carbon atoms and about 2 units of ethylene oxide, glycerol fatty acid esters comprising from about 14 to 30 carbon atoms and mixtures thereof. Most preferably the low HLB surfactants include cetyl, stearyl, cetostearyl or behenyl alcohols, steareth-2 and glycerol monostearate.

The second surfactant of the gel network thickener system may be anionic, or cationic. Anionic surfactants are selected from surfactants according to the formula $R_nX_mYM$, wherein R is a alkyl, alkenyl or alkylaryl group having from 8 to 30 carbon atoms, X is a polar group comprising at least one carbon atom and at least one oxygen or nitrogen atom, Y is an anionic group selected from carboxylates, sulphates, sulphonates or phosphates, n and m are independently 1 or 2 and M is hydrogen or a salt forming cation and mixtures thereof.

Representative examples of anionic surfactants include salts (such as alkaline salts, for example, sodium salts, ammonium salts, amine salts, amino alcohol salts and magnesium salts) of the following compounds: alkyl ether carboxylates, alkyl ether sulphates, alkyl glyceryl sulphonates, alkylamido ether sulphates, alkylarylpolyether sulphates, alkyl monoglyceride sulphates, alkyl ether sulphonates, alkylamide sulphonates; alkyl succinates, alkyl sulphosuccinates, alkyl ether sulphosuccinates, alkylamide sulphosuccinates; alkyl sulphosuccinamates; alkyl sulphoacetates; alkyl ether phosphates; acyl sarcosinates, N-acyl methylaminopropionate; acyl isethionates, N-acyltaurates; acyl lactylates; carboxyalkyl ether of alkyl polyglucosides; alkyl lecithin derivatives. The alkyl or acyl radical of all of these various compounds, for example, comprises from about 8 to 30 carbon atoms, and the aryl radical, for example, is chosen from phenyl and benzyl groups.

Preferably the anionic surfactants are selected from alkyl ether phosphates, alkyl ether sulphates, alkyl glyceryl sulphonates. N-acyl amino acid derivatives, N-acyl taurates, acyl lactylates and carboxyalkyl ether of alkyl polyglucosides. Yet more preferable surfactants are selected from alkyl ether phosphates having in average 1 to 20, preferably 1-10 and most preferably 1-3 ethylene oxide units.

The cationic surfactants suitable for use in the gel network thickener system are selected from quaternary ammonium salts or amido-amines having at least one fatty chain containing at least about 20 carbon atoms and mixture thereof.

The quaternary ammonium salts have general formula $N^+(R_1R_2R_3R_4)X^-$:

wherein, $R_1$ is selected from linear and branched radicals comprising about 20 to 30 carbon atoms, $R_1$ is selected from linear and branched radicals comprising about 20 to 30 carbon atoms or the same group as radicals $R_3$ to $R_4$, the radicals $R_3$ to $R_4$, which may be identical or different, are selected from linear and branched aliphatic radicals comprising from about 1 to 4 carbon atoms, and aromatic radicals such as aryl and alkylaryl, the aliphatic radicals may comprise at least one hetero atom such as oxygen, nitrogen, sulphur and halogens, the aliphatic radicals are chosen, for example, from alkyl, alkoxy and alkylamide radicals, and wherein X— is an anion selected from halides such as chloride, bromide and iodide) (C2-C6)alkyl sulphates, such as methyl sulphate, phosphates, alkyl and alkylaryl sulphonates, and anions derived from organic acids, such as acetate and lactate. The cationic surfactant is preferably selected from, for example, a behentrimonium chloride, behenamidopropyltrimonium methosulfate, stearamidopropyltrimonium chloride, arachidtrimonium chloride and mixtures thereof.

The amido-amine have general formula $R'_1$—CONH$(CH_2)nNR'_2R'_3$:

wherein, $R'_1$ is selected from linear and branched radicals comprising about 20 to 30 carbon atoms, the radicals $R'_2$ and $R'_3$, which may be identical or different, are selected from hydrogen, linear and branched aliphatic radicals comprising from about 1 to 4 carbon atoms, and aromatic radicals such as aryl and alkylaryl, the aliphatic radicals may comprise at least one hetero atom such as oxygen, nitrogen, sulphur and halogens, the aliphatic radicals are chosen, for example, from alkyl, alkoxy and alkylamide radicals, and wherein n is integer from 1 to 4. The amido-amine is preferably selected from, for example, behenamidopropyldimethylamine, behenamidopropyldiethylamine, behenamidoethyldiethylamine, behenamidoethyldimethylamine, arachidamidopropyldi methylamine, arachidamido-propyldiethylamine, arachidamidoethyldiethylamine, arachidamidoethyldimethylamine, and mixtures thereof.

The third surfactant of the gel network thickener system is a non-ionic surfactant. Non-ionic surfactants suitable for use in the gel network thickener system are selected from non-ionic surfactants having an HLB of 7 or more and comprising one or more polyethyleneoxide chains.

Representative examples of non-ionic surfactants comprising one or more polyethyleneoxide chains include the following compounds: polyoxyethylene alkyl ethers, polyethyleneglycol fatty acid esters, polyoxyethylene castor oil, polyoxyethylene hydrogenated castor oil, polyoxyethylene fatty amides and their momoethanolamine and diethanolamine derivatives and polyethoxylated fatty amines.

Preferred non-ionic surfactants include polyoxyethylene alkyl ethers or polyethylene glycol fatty acid esters having at least about 25, preferably from about 50 to 200, most preferably from about 100 to 200 ethylene oxide units, for example ceteareth-25, steareth-100, steareth-150 and steareth-200.

Particularly preferred gel network thickening systems according to the present invention include the ternary combination of fatty alcohols comprising from 14 to 30 carbon atoms, an anionic surfactant selected from C8-C30 alkyl ether phosphates having from 1 to 20, preferably 2 to 10 ethylene oxide units, and a non-ionic surfactant selected from polyoxyethylene alkyl ethers having at least 25, preferably from 100 to 200 ethylene oxide units.

More than one surfactant of each of the above specified types of the surfactants can be used. The compositions of the present invention may comprise a total amount of gel network forming surfactants from about 0.5% to about 30%, preferably from about 3% to about 20%, and more preferably from about 6% to about 15%. The compositions may comprises from 0.1 to 30%, preferably from 1 to 20% by weight of the low HLB surfactant, from 0.1 to 15%, preferably from 1 to 5% by weight of the ionic (i.e. anionic and or cationic surfactant) and 0.1 to 15%, preferably from 0.1 to 5% by weight of the non ionic surfactant. The preferred weight ratio low HLB surfactant or amphophile to ionic surfactant to non-ionic surfactant is from about 10:1:0.1 to about 10:10:10.

Polymers

The composition of the present invention may optionally further comprise at least about 0.01% of polymer. The polymer can be chosen, for example, from associative polymers, crosslinked acrylic acid homopolymers, crosslinked copolymers of (meth)acrylic acid and of (C1-C6)alkyl acrylate or polysaccharides. The polymer may serve as a thickening agent and also serve as conditioning agents, as described below. The polymer will generally be used at levels of from about 0.01% to about 20.0% by weight of the composition, preferably of from about 0.1% to about 5%.

Conditioning Agent

The compositions of the present invention may comprise or are used in combination with a composition comprising a conditioning agent. Conditioning agents suitable for use herein are selected from silicone materials, amino silicones, fatty alcohols, polymeric resins, polyol carboxylic acid esters, cationic polymers, cationic surfactants, insoluble oils and oil derived materials and mixtures thereof. Additional materials include mineral oils and other oils such as glycerin and sorbitol. Particularly useful conditioning materials are cationic polymers. Conditioners of cationic polymer type can be chosen from those comprising units of at least one amine group chosen from primary, secondary, tertiary and quaternary amine groups that may either form part of the main polymer chain, or be borne by a side substituent that is directly attached to the main polymer chain.

Silicones can be selected from polyalkylsiloxane oils, linear polydimethylsiloxane oils containing trimethylsilyl or hydroxydimethylsiloxane endgroups, polymethylphenylsiloxane, polydimethylphenylsiloxane or polydimethyldiphenylsiloxane oils, silicone resins, organofunctional siloxanes having in their general structure one or a number of organofunctional group(s), the same or different, attached directly to the siloxane chain or mixtures thereof. Said organofunctional group(s) are selected from: polyethyleneoxy and/or polypropyleneoxy groups, (per)fluorinated groups, thiol groups, substituted or unsubstituted amino groups, carboxylate groups, hydroxylated groups, alkoxylated groups, quaternium ammonium groups, amphoteric and betaine groups. The silicone can either be used as a neat fluid or in the form of a pre-formed emulsion.

The conditioning agent will generally be used at levels of from about 0.05% to about 20% by weight of the composition, preferably of from about 0.1% to about 15%, more preferably of from about 0.2% to about 10%, even more preferably of from about 0.2% to about 2%.

Chelants

According to the present invention, the compositions may comprise additional chelants.

Suitable additional chelants are additional amino-phosphonic acid chelants. Amino-Phosphonic acid chelants are defined as chelants comprising an amino-phosphonic acid moiety ($-PO_3H_2$) or its derivative $-PO_3R_2$ wherein $R_2$ is a $C_1$ to $C_6$ alkyl or aryl radical.

Suitable aminophosphonic acid type and aminophosphonic acid type derivatives include chelants according to the following formula (I):

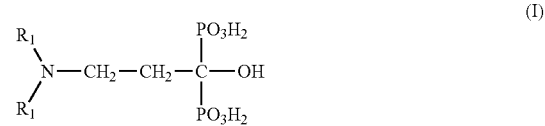

wherein each $R_1$ are independently selected from H or $C_1$-$C_3$ alkyl.

Other suitable aminophosphonic acid type chelants for use herein have the formula (II) below:

wherein each X are independently selected from hydrogen or alkyl radicals, preferably hydrogen or alkyl radicals having from 1 to 4 carbon atoms, preferably hydrogen; a, b and c are independently 1 to 4 and each $R_1$ are independently selected from $-PO_3H_2$ or a group having the formula (IIa) below:

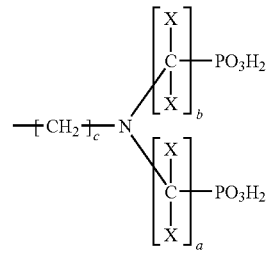

Wherein a, b and c are independently 1 to 4.

Preferred chelants according to Formula (II) for use herein are aminotri-(1-ethylphosphonic acid), ethylenediamine-tetra-(1-ethylphosphonic acid), aminotri-(1-propylphosphonic acid), aminotri-(isopropylphosphonic acid) and chelants having the formula (III) below:

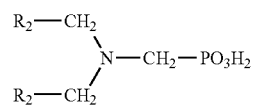

wherein each $R_2$ are independently selected from $-PO_3H_2$ or a group having the formula (IIIa) below:

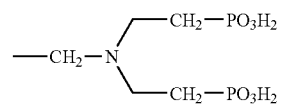

Especially preferred chelants according to formula (III) for use herein are aminotri-(methylenephosphonic acid), and ethylene-diamine-tetra-(methylenephosphonic acid) (EDTMP) and mixtures thereof.

According to the present invention, the oxidizing hair colourant compositions comprise from 0.01% to 5%, preferably from 0.25% to 3% more preferably from 0.25% to 1% of said amino-phosphonic acid type chelants, salts thereof, derivatives thereof and mixtures thereof.

Other examples of chelants suitable for use herein include EDDS (ethylenediaminedisuccinic acid), and carboxylic acids (in particular aminocarboxylic acids). Chelants may be incorporated into the composition of the present invention as stabilizers and or preservatives. In addition it has also been found that chelants provide hair fibre damage benefits and thus they may be utilized in order to further improve the hair damage profile of the present invention. Levels of chelants in the present invention may be as low as about 0.1%, preferably at least about 0.25%, more preferably about 0.5% for the most effective chelants such as diamine-N,N'-dipolyacid and monoamine monoamide-N,N'-dipolyacid chelants (for example EDDS). Less effective chelants will be more preferably used at levels of at least about 1%, even more preferably above about 2% by weight of the composition, depending of the efficiency of the chelant. Levels as high as about 10% can be used, but above this level significant formulation issues may arise.

Solvents

Suitable solvents for use in the compositions of the present invention include, but are not limited to water, butoxydiglycol, propylene glycol, alcohol (denat.), ethoxydiglycol, isopropylalcohol, hexylene glycol, benzyl alcohol and dipropylene glycol.

Finally, the compositions according to the present invention can be provided in any usual form, such as for example an aqueous composition, a powder, a gel or an oil-in-water emulsion. A preferred form for the compositions according to the present invention is thickened solutions comprising a salt-tolerant thickener or oil-in-water emulsions.

Method of Use

It is understood that the examples of methods of use and embodiments described herein are for illustrative purposes only and that various modifications or changes in light thereof will be suggested to one skilled in the art without departing from the scope of the present invention.

Oxidative hair dye compositions are usually sold in kits comprising, in individually packaged components such as separate containers, a dye component (also called "dye cream" for emulsions or "dye liquid" for solutions) comprising the oxidative dye precursors and alkalizing agent in a suitable carrier, and; a hydrogen peroxide component (also called "hydrogen peroxide cream" for emulsions or "hydrogen peroxide liquid" for solutions) comprising the oxidizing agent. The consumer mixes the dye component and hydrogen peroxide component together immediately before use and applies it onto the hair. The exemplified formulations given in the tables hereinafter illustrate these resulting mixtures.

The aminophosphonic acid type chelants of the present invention may be comprised within the dye component or the hydrogen peroxide component or both. Preferably the aminophosphonic acid type chelants are comprised in the dye component. If present, the additional chelant(s) such as EDDS, may also be present in the dye component and or the hydrogen peroxide component. Preferably however the additional chelants are also in the tint.

After working the mixture for a few minutes (to ensure uniform application to all of the hair), the oxidative dye or bleaching composition is allowed to remain on the hair for an amount sufficient for the dyeing to take place (usually about 2 to 60 minutes preferably from about 30 to 45 minutes). The consumer then rinses his/her hair thoroughly with water and allows it to dry. It is observed that the hair has changed from its original color to the desired color.

When present in the oxidative dye composition, the optional conditioning agent can be provided in a third container. In the latter case, all three compositions can be mixed immediately before use and applied together, or the content of the third container can be applied (after an optional rinse step) as a post-treatment immediately after the oxidative dye composition resulting from the mixture of the other containers.

According to one method for oxidatively colouring hair according to the present invention, the method comprises the steps of applying an oxidising hair colouring composition of the present invention to the hair and subsequently removing the composition from the hair.

According to the present invention the methods of colouring hair also comprise embodiments whereby the composition of the present invention is applied to the hair and preferably the mixture is worked for a few minutes (to ensure uniform application to all of the hair). The composition is then allowed to remain on the hair in order for the colour to develop for a time period of less than about 20 minutes, preferably less than about 15 minutes, more preferably from about 5 minutes to about 10 minutes, most preferably for about 10 minutes. The consumer then rinses his/her hair thoroughly with tap water and allows it to dry and or styles the hair as usual.

According to a further alternative embodiment of the present invention, the method of colouring the hair is a sequential oxidative hair colouring method comprising the steps of at least two sequential oxidative hair colour treatments wherein the time period between each treatment is from 1 to 60 days, preferably from 1 to 40 days, more preferably from 1 to 28 days, even more preferably from 1 to 14 days and most preferably from 1 to 7 days. In such embodiments the time that the composition is retained on head may be less than about 20 minutes and is preferably less than about 10 minutes and most preferably from about 2 minutes to about 5 minutes.

The aminophosphonic acid type chelants of the present invention may also be applied to hair as a pre-treatment. The pretreatment composition ("first composition") can be applied immediately before the oxidizing composition comprising an oxidizing agent and at least one primary intermediate (developer) and at least one coupler selected from 4-amino-2-hydroxytoluene, 2-methyl-5-hydroxyethylaminophenol, 2,4-diaminophenoxyethanol, 6-hydroxybenzomorpholine, 1-napthol and mixtures thereof ("second composition") or after a longer period of time. In the case of a pretreatment applied on hair and immediately followed by the oxidizing composition, said pretreatment composition can be rinsed off hair before the application of the oxidizing composition, but will be preferably kept on the hair during the application of the oxidizing compositions, the resulting mixture being rinsed off following the oxidizing step. Kits comprising one container for the first composition (pre-treat) and one, two or more containers for the second composition (oxidizing composition) can be advantageously used for this method. Two containers or more can be required for the second composition in case this second composition is prepared immediately before use by mixing the content of two containers or more (e.g. oxidative hair dye composition). The kit can also comprise an additional container for a composition comprising a conditioning agent that is applied independently from the second composition in a third step, optionally following a rinsing step.

The kits described hereinabove are well known in the art and the composition in each container can be manufactured utilizing any one of the standard approaches, these include a) 'Oil in water' process, b) 'Phase Inversion' process and c) 'One-pot' process.

For example, in a 'One-pot' process, the polymers and chelants would be pre-dissolved in water, the fatty materials added and then the whole composition heated to about 70-80° C. A controlled cooling and optional shearing process to form the final structured product in the case of an emulsion would then follow. Addition of the materials providing source of peroxymonocarbonate ions, dyes, amino-phosphonic acid type chelants and ammonia, and optionally solvents, and pH trimming complete the making process of the dye cream.

In the case of a liquid solution comprising acrylate polymers, these would be formulated into the hydrogen peroxide component. The glycol solvents and fatty components are formulated into the dye component. A structured product is formed when the dye and hydrogen peroxide components are mixed together prior to use of the composition, resulting from deprotonation of the polymer acrylic acid groups as the pH rises, yielding a polymeric micro-gel. Further details on the manufacture of these two-part aqueous composition for coloring hair, which forms a gel on mixing of the two parts can be found in U.S. Pat. No. 5,376,146, Casperson et al. and U.S. Pat. No. 5,393,305, Cohen et al.

The composition of the present invention can also be formulated as 2-part aqueous compositions comprising polyetherpolyurethane as thickening agent (such as Aculyn® 46) as described in U.S. Pat. No. 6,156,076. Casperson et al. and U.S. Pat. No. 6,106,578, Jones.

The present invention may be utilized in a variety of packaging and dispensing devices. These dispensing devices can come in the form of separate devices which may be used independently or in combination with one another. Typically, the hair colouring or bleaching compositions are contained within separate single or multi compartment containers so that the compositions can be stored separately from one another before use. The compositions are then mixed together by a mixing means and then applied to the consumer's hair by an application means.

The most common packaging device which can be used for the present invention involves storing the developer in a container such as a bottle, tube, aerosol, or a sachet and separately storing the dye lotion in an additional compartment within the developer container or in a separate container which may be identical such as a dual sachet or aerosol system, for example or different such as a bottle and tube system.

The consumer may mix the developer lotion and the dye lotion by any means. This may simply involve the use of a mixing bowl into which the lotions are dispensed and then mixed, preferably using a mixing means such as a tool. Alternatively it may involve the addition of one of the lotions into the container of the other lotion, (typically the dye lotion is added to the developer lotion), followed by manual shaking or mixing with a tool. Another system involves the perforation or displacement of a seal located between the separate compartments of the dye and developer lotion within a single container or sachet followed by manual mixing within the container or in a separate and or additional container.

An example of such devices are the so called 'twist and go' devices. These devices allow the consumer to twist the base of a container holding the dye which enables a communication port to open that exposes the base of the bottle holding the dye and the top of the bottle holding the developer. The two components are mixed and the consumer dispenses the product by squeezing the flexible top portion of the bottle for dispensing.

Alternatively more complex devices may be utilised, whereby the lotions are mixed upon actuation of dispensing. An example of such as a complex system is a dual aerosol system e.g. bag-in-can or piston. The dye and developer are stored separately in two aerosol cans within one device, a propellant being used to pressurize the contents of the can or bag in can or piston and a valve providing the control of dispensation. When the consumer actuates the valve, the dye and developer are dispensed simultaneously out of the cans and are mixed together via a static mixer just before dispensing the product onto the hair. The ratio of the dye and developer can be manipulated by the viscosity of the products, the can pressure, or by altering the flow channel sizes through the valve. Additionally, the product can be foamed and delivered via a mousse form.

Another example of such a complex system utilises a dual piston screw system. The dye and the developer are kept in separate piston cylinder systems within the system and when the consumer actuates a button, two screws are rotated such that the dual pistons inside pressurize the liquid in the cylinders and thus force the products to move through a mixing station and out of the nozzle for dispensing. The ratios of the dye and the developer can be manipulated by the diameter of the cylinder of the package. Additionally, an in line static mixer can be used to aid mixing and such a system can be completely disposable or completely refillable.

Yet another system utilises one or more manually actuated pumps. The product may be premixed in a collapsible sachet. When the consumer actuates the pump, the liquid inside the pump is dispensed. As the manually actuated pump returns to the upright position it forces product from a collapsible sachet. Alternatively, a dual system can be installed whereby two sachets and two pumps are used to deliver the dye and the developer lotions to the hair. Alternatively, a single pump connected to two sachets can deliver the product by incorporating the mixing point within the pump. Another embodiment uses a rigid bottle and a dip tube to connect the product to the pump system. Finally, a delaminating bottle can be used in combination with a manually actuated pump where the inner layer of the bottle separates from the outer layer of the bottle which forces the contents of the bottle to be emptied.

Typically these complex systems offer the advantage of product application independently of the orientation of the product.

The devices described herein above can also be used in combination with a product delivery and or application tool to aid application of the product onto the hair. Again these devices may be of a very simple nature such as a nozzle attached to one of the containers or a separate applicator device such as a comb or brush. Such combs and brushes can be adapted in order to achieve particular effects, whether it be quick and even coverage or root/hairline touch up, or highlights or streaks. Alternatively, the container or one of the containers may be provided with a comb attached to or instead of the dispensing nozzle whereby the product is dispensed through hollow tines and dispensing apertures located in the comb tines. The comb tines may be provided with single or multiple openings along the tines to improve product application and evenness especially root to tip. Product dispensation can be achieved by mechanical pressure applied to the container for example delaminating bottles or any of the mechanisms described hereinabove. The comb may be provided on the container such as to facilitate easy application and may be positioned vertically (so called verticomb) or at an angle to allow the consumer to access all areas. All devices may be designed to have inter-changeability, so that a range of different tools for hair application can be provided to the consumer.

The application devices may also include devices which assist in achieving particular effects such as highlighting such as highlighting combs, brushes and tools, foils and highlighting caps.

Additional device technology can be used to assist in the penetration of the product into the hair. Examples of such technology include heating devices, ultraviolet light devices and ultrasound devices.

EXAMPLES

The following examples illustrate oxidative colouring compositions according to the present invention and methods of manufacture thereof. It is understood that the examples and embodiments described herein are for illustrative purposes only and that various modifications or changes in light thereof will be suggested to one skilled in the art without departing from the scope of the present invention.

Example Formulations

|  | 1 | 2 |
|---|---|---|
| Sodium sulphite | 0.1 | 0.1 |
| Ascorbic Acid | 0.2 | 0.2 |
| Ethylenediaminetetracetic acid, disodium salt | 0.03 | 0.03 |
| Citric Acid | 0.2 | 0.2 |
| Ammonia(30% active) | 4.0 | 4.0 |
| Acrylates Copolymer(Aculyn ® 33A) | 1.0 | 1.0 |
| Oleth 5 | 0.5 | 0.5 |
| Oleth 2 | 1.0 | 1.0 |
| Oleic Acid | 0.9 | 0.9 |
| Cocamidopropyl betaine | 3.0 | 3.0 |
| Etidronic Acid | 0.05 | 0.05 |
| Isopropyl alcohol | 2.5 | 2.5 |
| Hydrogen Peroxide (35% active) | 8.6 | 13 |
| Soytrimonium Chloride and propylene glycol | 3.0 | 3.0 |
| Simethicone | 0.003 | 0.003 |
| Steareth-21 | 1.0 | 1.0 |
| PEG-50 Hydrogenated Palmamide | 0.5 | 0.5 |
| Oleyl Alcohol | 0.2 | 0.2 |
| Acrylates Steareth-20 Methacrylate Copolymer(Aculyn ® 22) | 0.5 | 1.0 |
| Propylene Glycol | 2.0 | 2.0 |
| Ethoxy Diglycol | 4.2 | 4.2 |
| C11-15 Pareth-9 | 0.5 | 0.5 |
| C12-15 Pareth-3 | 0.8 | 0.8 |
| Diethylene-triamine-penta(methylene phosphonic) acid | 0.5 | 1.0 |
| p-phenylene diamine | 0.6 | 0.6 |
| 4-amino-2-hydroxytoluene | 0.6 | 0.6 |
| p-amino phenol | 0.25 | 0.25 |
| 1-napthol | 0.3 | 0.3 |
| 2-methyl-5-hydroxyethylaminophenol | 0.2 | 0.2 |
| pH adjust to pH 10 | qs | qs |
| Water | qs | qs |

| Ingredient | Formulation 3 | Formulation 4 |
|---|---|---|
| Sodium sulphite | 0.1 | 0.1 |
| Ascorbic Acid | 0.1 | 0.1 |
| Ammonium Carbonate | 5.0 | 6.0 |
| Potassium Hydrogen Carbonate | 0.1 | 0.1 |
| Ammonium Acetate | 0.2 | 0.2 |
| Crodafos ® CES | 2.0 | 3.0 |
| Ceteareth-25 (Volpo CS25) | 1.0 | — |
| Stearyl Alcohol | 2.0 | — |
| Sodium Hydroxide (50% Solution) | 0.3 | 0.3 |
| tetrasodium salt of Ethylenediaminetetraacetic acid | 0.1 | 0.1 |
| Etidronic Acid | 0.5 | 0.5 |
| Hydrogen Peroxide (35% active) | 8.6 | 8.6 |
| Amodimethicone (Belsil ADM1100) | — | 1.0 |
| Polyquaternium-22 (Merquat 295) | 0.2 | — |
| Polyquaternium-37 & Mineral oil (Salcare SC95) | 0.2 | — |
| Styrene-PVP Copolymer(Polectron 430) | 0.1 | 0.5 |
| Xanthan gum | 0.1 | — |
| Acrylates/C10-30 Alkyl Acrylate Crosspolymer |  |  |
| Cetyl Alcohol |  |  |
| Acrylates Steareth-20 Methacrylate Copolymer (Aculyn ® 22) | 0 | 1.0 |
| Acrylates copolymer (Aculyn 33) | 1.0 | 1.0 |
| Diethylene-triamine-penta(methylene phosphonic) acid | 0.25 |  |
| p-phenylene diamine | 0.6 | 0.6 |
| 4-amino-2-hydroxytoluene | 0.2 | 0.2 |
| 2,4-diaminophenoxyethanol dihydrochloride | 0.1 | 0.1 |
| p-amino phenol | 0.3 | 0.3 |
| Hydroxybenzomorpholine | 0.2 | 0.2 |
| 1-napthol | 0.2 | 0.2 |
| 2-methyl-5-hydroxyethylaminophenol | 0.02 | 0.02 |
| pH adjust to pH 9.0 | Qs | Qs |
| Water | Qs | Qs |

|  | Formulation 5 | Formulation 6 |
|---|---|---|
| Sodium sulphite | 0.1 | 0.1 |
| Ascorbic Acid | 0.2 | 0.2 |
| Ethylenediaminetetracetic acid, disodium salt | 0.03 | 0.03 |
| Ammonia(30% active) | 4.0 | 4.0 |
| Cetearyl Alcohol | 12.0 | 12.0 |
| Sodium Lauryl Sulfate | 2.0 | 2.0 |
| Glyceral Stearate | 2.5 | 2.5 |
| Glycol Distearate | 1.5 | 1.5 |
| Lanolin Alcohol | 0.5 | 0.5 |
| Sodium Cocoyl Isethionate | 1.8 | 1.8 |
| Hydrogen Peroxide (35% active) | 8.6 | 13 |
| Etidronic acid | 0.1 | 0.1 |
| Cellulose Gum | 0.1 | 0.1 |
| PEG-40 Stearate | 0.75 | 0.75 |
| Sorbitan Stearate | 0.5 | 0.5 |
| Diethylene-triamine-penta(methylene phosphonic) acid | 0.5 | 0.0 |
| Ethylene-diaminetatra-(1-ethylphosphonic acid) | 0.5 | 1.0 |
| p-phenylene diamine | 0.6 | 0.6 |
| 4-amino-2-hydroxytoluene | 0.6 | 0.6 |
| p-amino phenol | 0.25 | 0.25 |
| 1-napthol | 0.3 | 0.3 |
| Hydroxybenzomorpholine | 0.2 | 0.2 |
| 2-methyl-5-hydroxyethylaminophenol | 0.2 | 0.2 |
| pH adjust to pH 10 | qs | qs |
| Water | qs | qs |

Example Formulations 7-12

|  | 7 | 8 | 9 | 10 | 11 | 12 |
|---|---|---|---|---|---|---|
| Sodium sulphite | 0.1 | 0.1 | 0.1 | 0.1 | 0.1 | 0.1 |
| Ascorbic Acid | 0.2 | 0.2 | 0.2 | 0.2 | 0.2 | 0.2 |
| Ethylenediaminetetracetic acid, disodium salt | 0.03 | 0.03 | 0.03 | 0.03 | 0.03 | 0.03 |
| Citric Acid | 0.2 | 0.2 | 0.2 | 0.2 | 0.2 | 0.2 |
| Ammonia (30% active) | 4.0 | 4.0 | 4.0 | 4.0 | 4.0 | 4.0 |
| Acrylates Copolymer (Aculyn ® 33A) | 1.0 | 1.0 | 1.0 | 1.0 | 1.0 | 1.0 |
| Oleth 5 | 0.5 | 0.5 | 0.5 | 0.5 | 0.5 | 0.5 |

-continued

|  | 7 | 8 | 9 | 10 | 11 | 12 |
|---|---|---|---|---|---|---|
| Oleth 2 | 1.0 | 1.0 | 1.0 | 1.0 | 1.0 | 1.0 |
| Oleic Acid | 0.9 | 0.9 | 0.9 | 0.9 | 0.9 | 0.9 |
| Cocamidopropyl betaine | 3.0 | 3.0 | 3.0 | 3.0 | 3.0 | 3.0 |
| Etidronic Acid | 0.05 | 0.05 | 0.05 | 0.05 | 0.05 | 0.05 |
| Isopropyl alcohol | 2.5 | 2.5 | 2.5 | 2.5 | 2.5 | 2.5 |
| Hydrogen Peroxide (35% active) | 8.6 | 17.2 | 8.6 | 17.2 | 8.6 | 17.2 |
| Soytrimonium Chloride and propylene glycol | 3.0 | 3.0 | 3.0 | 3.0 | 3.0 | 3.0 |
| Simethicone | 0.003 | 0.003 | 0.003 | 0.003 | 0.003 | 0.003 |
| Steareth-21 | 1.0 | 1.0 | 1.0 | 1.0 | 1.0 | 1.0 |
| PEG-50 Hydrogenated Palmamide | 0.5 | 0.5 | 0.5 | 0.5 | 0.5 | 0.5 |
| Oleyl Alcohol | 0.2 | 0.2 | 0.2 | 0.2 | 0.2 | 0.2 |
| Acrylates Steareth-20 Methacrylate Copolymer (Aculyn ® 22) | 0.5 | 1.0 | 0.5 | 1.0 | 0.5 | 1.0 |
| Propylene Glycol | 2.0 | 2.0 | 2.0 | 2.0 | 2.0 | 2.0 |
| Ethoxy Diglycol | 4.2 | 4.2 | 4.2 | 4.2 | 4.2 | 4.2 |
| C11-15 Pareth-9 | 0.5 | 0.5 | 0.5 | 0.5 | 0.5 | 0.5 |
| C12-15 Pareth-3 | 0.8 | 0.8 | 0.8 | 0.8 | 0.8 | 0.8 |
| Diethylene-triamine-penta(methylene phosphonic) acid | 0.5 | 1.0 | 0.5 | 1.0 | — | — |
| Ethylene Diamine Di Succinate | — | — | 1.0 | 3.0 | 1.0 | 3.0 |
| p-Phenylenediamine | 0.6 | 0.6 | 0.6 | 0.6 | 0.6 | 0.6 |
| 4-Amino-2-hydroxytoluene | 0.2 | 0.2 | 0.2 | 0.2 | 0.2 | 0.2 |
| p-Aminophenol | 0.25 | 0.25 | 0.25 | 0.25 | 0.25 | 0.25 |
| 1-Naphthol | 0.3 | 0.3 | 0.3 | 0.3 | 0.3 | 0.3 |
| Resorcinol | 0.2 | 0.2 | 0.2 | 0.2 | 0.2 | 0.2 |
| 2-methyl resorcinol | 0.1 | 0.1 | 0.1 | 0.1 | 0.1 | 0.1 |
| m-aminophenol | 0.4 | 0.4 | 0.4 | 0.4 | 0.4 | 0.4 |
| 3-amino-2,6-dimethyl phenol | 0.2 | 0.2 | 0.2 | 0.2 | 0.2 | 0.2 |
| 2-methyl-5-hydroxyethylaminophenol | 0.1 | 0.1 | 0.1 | 0.1 | 0.1 | 0.1 |
| 1-acetoxy-2-methylnaphthalene | 0.3 | 0.3 | 0.3 | 0.3 | 0.3 | 0.30 |
| 2-amino-3-hydroxypyridine | 0.0 | 0.1 | 0.0 | 0.1 | 0.0 | 0.3 |
| 2-amino-4-hydroxyethylaminoanisole | 0.1 | 0.1 | 0 | 0 | 0 | 0 |
| Phenyl methyl pyrazolone | 0.1 | 0.1 | 0.1 | 0.1 | 0.1 | 0.1 |
| 4-chlororesorcinol | 0.1 | 0.1 | 0.1 | 0.1 | 0.1 | 0.1 |
| 1,3-bis(2,4-diaminophenoxy)propane HCl | 0 | 0 | 0.1 | 0.1 | 0 | 0 |
| 5-Amino-6-chloro-o-cresol | 0.05 | 0.05 | 0.05 | 0.05 | 0.05 | 0.05 |
| 5-Amino-4-chloro-o-cresol | 0 | 0 | 0 | 0.2 | 0.2 | 0.2 |
| 6-Methoxy-2-methylamino-3-aminopyridine HCl | 0 | 0 | 0 | 0 | 0.05 | 0.05 |
| 2,6-Dimethoxy-3,5-Pyridinediamine HCl | 0 | 0 | 0 | 0 | 0.05 | 0.05 |
| 2-Amino-6-chloro-4-nitrophenol | 0.1 | 0.1 | 0.1 | 0 | 0 | 0 |
| 2-hydroxyethylpicramic acid | 0.1 | 0.1 | 0.1 | 0 | 0 | 0 |
| N-(2-Hydroxyethyl)-2-Nitro-4-Trifluoromethylaniline | 0 | 0 | 0 | 0.1 | 0.1 | 0.1 |
| 1-Amino-5-chloro-4-(2,3-Dihydroxypropylamino)-2-Nitrobenzene & 3,3'-1[(2-Chloro-5-Nitro,1,4-Phenylene)Diimino]Bis-1,2-Propanediol | 0 | 0 | 0 | 0.1 | 0.1 | 0.1 |
| pH adjust to pH 10 | qs | qs | qs | qs | qs | qs |
| Water | qs | qs | qs | qs | qs | qs |

Example Formulations 12-18

|  | 13 | 14 | 15 | 16 | 17 | 18 |
|---|---|---|---|---|---|---|
| Sodium sulphite | 0.1 | 0.1 | 0.1 | 0.1 | 0.1 | 0.1 |
| Ascorbic Acid | 0.2 | 0.2 | 0.2 | 0.2 | 0.2 | 0.2 |
| Ethylenediaminetetracetic acid, disodium salt | 0.03 | 0.03 | 0.03 | 0.03 | 0.03 | 0.03 |
| Citric Acid | 0.2 | 0.2 | 0.2 | 0.2 | 0.2 | 0.2 |
| Ammonia (30% active) | 4.0 | 4.0 | 4.0 | 4.0 | 4.0 | 4.0 |
| Acrylates Copolymer (Aculyn ® 33A) | 1.0 | 1.0 | 1.0 | 1.0 | 1.0 | 1.0 |
| Oleth 5 | 0.5 | 0.5 | 0.5 | 0.5 | 0.5 | 0.5 |
| Oleth 2 | 1.0 | 1.0 | 1.0 | 1.0 | 1.0 | 1.0 |
| Oleic Acid | 0.9 | 0.9 | 0.9 | 0.9 | 0.9 | 0.9 |
| Cocamidopropyl betaine | 3.0 | 3.0 | 3.0 | 3.0 | 3.0 | 3.0 |
| Etidronic Acid | 0.05 | 0.05 | 0.05 | 0.05 | 0.05 | 0.05 |
| Isopropyl alcohol | 2.5 | 2.5 | 2.5 | 2.5 | 2.5 | 2.5 |
| Hydrogen Peroxide (35% active) | 8.6 | 17.2 | 8.6 | 17.2 | 8.6 | 17.2 |

-continued

|  | 13 | 14 | 15 | 16 | 17 | 18 |
|---|---|---|---|---|---|---|
| Soytrimonium Chloride and propylene glycol | 3.0 | 3.0 | 3.0 | 3.0 | 3.0 | 3.0 |
| Simethicone | 0.003 | 0.003 | 0.003 | 0.003 | 0.003 | 0.003 |
| Steareth-21 | 1.0 | 1.0 | 1.0 | 1.0 | 1.0 | 1.0 |
| PEG-50 Hydrogenated Palmamide | 0.5 | 0.5 | 0.5 | 0.5 | 0.5 | 0.5 |
| Oleyl Alcohol | 0.2 | 0.2 | 0.2 | 0.2 | 0.2 | 0.2 |
| Acrylates Steareth-20 Methacrylate Copolymer (Aculyn ® 22) | 0.5 | 1.0 | 0.5 | 1.0 | 0.5 | 1.0 |
| Propylene Glycol | 2.0 | 2.0 | 2.0 | 2.0 | 2.0 | 2.0 |
| Ethoxy Diglycol | 4.2 | 4.2 | 4.2 | 4.2 | 4.2 | 4.2 |
| C11-15 Pareth-9 | 0.5 | 0.5 | 0.5 | 0.5 | 0.5 | 0.5 |
| C12-15 Pareth-3 | 0.8 | 0.8 | 0.8 | 0.8 | 0.8 | 0.8 |
| Diethylene-triamine-penta(methylene phosphonic) acid | 0.5 | 1.0 | 0.5 | 1.0 | — | — |
| Ethylene Diamine Di Succinate | — | — | 1.0 | 3.0 | 1.0 | 3.0 |
| p-Phenylenediamine | 0.6 | 0.6 | 0.6 | 0.6 | 0.6 | 0.6 |
| 4-Amino-2-hydroxytoluene | 0.6 | 0.6 | 0.6 | 0.6 | 0.6 | 0.6 |
| p-Aminophenol | 0.25 | 0.25 | 0.25 | 0.25 | 0.25 | 0.25 |
| 1-Naphthol | 0.3 | 0.3 | 0.3 | 0.3 | 0.3 | 0.3 |
| Resorcinol | 0.2 | 0.2 | 0.2 | 0.2 | 0.2 | 0.2 |
| 2-methyl resorcinol | 0.1 | 0.1 | 0.1 | 0.1 | 0.1 | 0.1 |
| m-aminophenol | 0.4 | 0.4 | 0.4 | 0.4 | 0.4 | 0.4 |
| 3-amino-2,6-dimethyl phenol | 0.2 | 0.2 | 0.2 | 0 | 0 | 0 |
| 2-methyl-5-hydroxyethylaminophenol | 0.2 | 0.2 | 0.2 | 0.2 | 0.2 | 0.2 |
| 1-acetoxy-2-methylnaphthalene | 0.3 | 0.3 | 0.3 | 0.3 | 0.3 | 0.30 |
| 2-amino-3-hydroxypyridine | 0.0 | 0.1 | 0.0 | 0.1 | 0.0 | 0.3 |
| 2-amino-4-hydroxyethylaminoanisole | 0.1 | 0.1 | 0 | 0 | 0 | 0 |
| Phenyl methyl pyrazolone | 0.1 | 0.1 | 0.1 | 0.1 | 0.1 | 0.1 |
| 4-chlororesorcinol | 0.1 | 0.1 | 0.1 | 0.1 | 0.1 | 0.1 |
| 1,3-bis(2,4-diaminophenoxy)propane HCl | 0 | 0 | 0.1 | 0.1 | 0 | 0 |
| 5-Amino-6-chloro-o-cresol | 0.05 | 0.05 | 0.05 | 0.05 | 0.05 | 0.05 |
| 5-Amino-4-chloro-o-cresol | 0 | 0 | 0 | 0.2 | 0.2 | 0.2 |
| 6-Methoxy-2-methylamino-3-aminopyridine HCl | 0 | 0 | 0 | 0 | 0.1 | 0.1 |
| 2,6-Dimethoxy-3,5-Pyridinediamine HCl | 0 | 0 | 0 | 0 | 0.1 | 0.1 |
| Hydroxyethyl-2-Nitro-p-Toluidine | 0.1 | 0.1 | 0.1 | 0 | 0 | 0 |
| 2-amino-4,6-dinitrophenol | 0.1 | 0.1 | 0.1 | 0 | 0 | 0 |
| 3-nitro-p-hydroxyethylaminophenol | 0 | 0 | 0 | 0.1 | 0.1 | 0.1 |
| 4-hydroxypropylamino-3-nitrophenol | 0 | 0 | 0 | 0.1 | 0.1 | 0.1 |
| pH adjust to pH 10 | qs | qs | qs | qs | qs | qs |
| Water | qs | qs | qs | qs | qs | qs |

Example Formulations 19-24

|  | 19 | 20 | 21 | 22 | 23 | 24 |
|---|---|---|---|---|---|---|
| Sodium sulphite | 0.1 | 0.1 | 0.1 | 0.1 | 0.1 | 0.1 |
| Ascorbic Acid | 0.1 | 0.1 | 0.1 | 0.1 | 0.1 | 0.1 |
| Ammonium Carbonate | 5.0 | 6.0 | 3.0 | 2.0 | 5.0 | 6.0 |
| Potassium Hydrogen Carbonate | 0.1 | 0.1 | 0.1 | 0.1 | 0.1 | 0.1 |
| Ammonium Acetate | 0.2 | 0.2 | 0.2 | 0.2 | 0.2 | 0.2 |
| Crodafos ® CES | 2.0 | 3.0 | 2.0 | 3.0 | 2.0 | 3.0 |
| Ceteareth-25 (Volpo CS25) | 1.0 | — | 1.0 | — | 1.0 | — |
| Stearyl Alcohol | 2.0 | — | 2.0 | — | 2.0 | — |
| Sodium Hydroxide (50% Solution) | 0.3 | 0.3 | 0.3 | 0.3 | 0.3 | 0.3 |
| EDTA (Tetrasodium Salt) | 0.1 | 0.1 | 0.1 | 0.1 | 0.1 | 0.1 |
| Etidronic Acid | 0.5 | 0.5 | 0.5 | 0.5 | 0.5 | 0.5 |
| Hydrogen Peroxide (35% Active) | 8.6 | 17.2 | 8.6 | 17.2 | 8.6 | 17.2 |
| Amodimethicone (Belsil ADM1100) | — | 1.0 | — | 1.0 | — | 1.0 |
| Polyquaternium-22 (Merquat 295) | 0.2 | — | 0.2 | — | 0.2 | — |
| Polyquaternium-37 & Mineral Oil (Salcare SC95) | 0.2 | — | 0.2 | — | 0.2 | — |
| Styrene-PVP Copolymer (Polectron 430) | 0.1 | 0.5 | 0.1 | 0.5 | 0.1 | 0.5 |
| Xanthan Gum | 0.1 | — | 0.1 | — | 0.1 | — |
| Acrylates/C10-30 Alkyl Acrylate Crosspolymer | — | 0.5 | — | 0.5 | — | 0.5 |
| Cetyl Alcohol | 2.0 | — | 2.0 | — | 2.0 | — |
| Acrylates Steareth-20 Methacrylate Copolymer (Aculyn 22) | 0 | 1.0 | 0 | 1.0 | 0 | 1.0 |
| Acrylates copolymer (Aculyn 33) | 1.0 | 1.0 | 1.0 | 1.0 | 1.0 | 1.0 |

|  | 19 | 20 | 21 | 22 | 23 | 24 |
|---|---|---|---|---|---|---|
| Steareth-200 | 1.0 | 1.0 | 1.0 | 1.0 | 1.0 | 1.0 |
| Propylene Glycol | 3.0 | 3.0 | 3.0 | 3.0 | 3.0 | 3.0 |
| Diethylene-triamine-penta(methylene phosphonic) acid | 0.5 | 1.0 | 0.5 | 1.0 | — | — |
| Ethylene Diamine Di Succinate | — | — | 1.0 | 3.0 | 1.0 | 3.0 |
| p-Phenylenediamine | 0.6 | 0.6 | 0.6 | 0.6 | 0.6 | 0.6 |
| 4-Amino-2-hydroxytoluene | 0.2 | 0.2 | 0.2 | 0.2 | 0.2 | 0.2 |
| p-Aminophenol | 0.25 | 0.25 | 0.25 | 0.25 | 0.25 | 0.25 |
| 1-Naphthol | 0.3 | 0.3 | 0.3 | 0.3 | 0.3 | 0.3 |
| Resorcinol | 0.2 | 0.2 | 0.2 | 0.2 | 0.2 | 0.2 |
| 2-methyl resorcinol | 0.1 | 0.1 | 0.1 | 0.1 | 0.1 | 0.1 |
| m-aminophenol | 0.4 | 0.4 | 0.4 | 0.4 | 0.4 | 0.4 |
| 3-amino-2,6-dimethyl phenol | 0.2 | 0.2 | 0.2 | 0.2 | 0.2 | 0.2 |
| 2-methyl-5-hydroxyethylaminophenol | 0.1 | 0.1 | 0.1 | 0.1 | 0.1 | 0.1 |
| 1-acetoxy-2-methylnaphthalene | 0.3 | 0.3 | 0.3 | 0.3 | 0.3 | 0.30 |
| 2-amino-3-hydroxypyridine | 0.0 | 0.1 | 0.0 | 0.1 | 0.0 | 0.3 |
| 2-amino-4-hydroxyethylaminoanisole | 0.1 | 0.1 | 0 | 0 | 0 | 0 |
| Phenyl methyl pyrazolone | 0.1 | 0.1 | 0.1 | 0.1 | 0.1 | 0.1 |
| 4-chlororesorcinol | 0.1 | 0.1 | 0.1 | 0.1 | 0.1 | 0.1 |
| 1,3-bis(2,4-diaminophenoxy)propane HCl | 0 | 0 | 0.1 | 0.1 | 0 | 0 |
| 5-Amino-6-chloro-o-cresol | 0.05 | 0.05 | 0.05 | 0.05 | 0.05 | 0.05 |
| 5-Amino-4-chloro-o-cresol | 0 | 0 | 0 | 0.2 | 0.2 | 0.2 |
| 6-Methoxy-2-methylamino-3-aminopyridine HCl | 0 | 0 | 0 | 0 | 0.05 | 0.05 |
| 2,6-Dimethoxy-3,5-Pyridinediamine HCl | 0 | 0 | 0 | 0 | 0.05 | 0.05 |
| 2-Amino-6-chloro-4-nitrophenol | 0.1 | 0.1 | 0.1 | 0 | 0 | 0 |
| 2-hydroxyethylpicramic acid | 0.1 | 0.1 | 0.1 | 0 | 0 | 0 |
| N-(2-Hydroxyethyl)-2-Nitro-4-Trifluoromethylaniline | 0 | 0 | 0 | 0.1 | 0.1 | 0.1 |
| 1-Amino-5-chloro-4-(2,3-Dihydroxypropylamino)-2-Nitrobenzene & 3,3'-[(2-Chloro-5-Nitro,1,4-Phenylene)Diimino]Bis-1,2-Propanediol | 0 | 0 | 0 | 0.1 | 0.1 | 0.1 |
| pH adjust to pH 9.0 | qs | qs | qs | qs | qs | qs |
| Water | qs | qs | qs | qs | qs | qs |

Example Formulations 25-30

|  | 25 | 26 | 27 | 28 | 29 | 30 |
|---|---|---|---|---|---|---|
| Sodium sulphite | 0.1 | 0.1 | 0.1 | 0.1 | 0.1 | 0.1 |
| Ascorbic Acid | 0.1 | 0.1 | 0.1 | 0.1 | 0.1 | 0.1 |
| Ammonium Carbonate | 5.0 | 6.0 | 3.0 | 2.0 | 5.0 | 6.0 |
| Potassium Hydrogen Carbonate | 0.1 | 0.1 | 0.1 | 0.1 | 0.1 | 0.1 |
| Ammonium Acetate | 0.2 | 0.2 | 0.2 | 0.2 | 0.2 | 0.2 |
| Crodafos ® CES | 2.0 | 3.0 | 2.0 | 3.0 | 2.0 | 3.0 |
| Ceteareth-25 (Volpo CS25) | 1.0 | — | 1.0 | — | 1.0 | — |
| Stearyl Alcohol | 2.0 | — | 2.0 | — | 2.0 | — |
| Sodium Hydroxide (50% Solution) | 0.3 | 0.3 | 0.3 | 0.3 | 0.3 | 0.3 |
| EDTA (Tetrasodium Salt) | 0.1 | 0.1 | 0.1 | 0.1 | 0.1 | 0.1 |
| Etidronic Acid | 0.5 | 0.5 | 0.5 | 0.5 | 0.5 | 0.5 |
| Hydrogen Peroxide (35% Active) | 8.6 | 17.2 | 8.6 | 17.2 | 8.6 | 17.2 |
| Amodimethicone (Belsil ADM1100) | — | 1.0 | — | 1.0 | — | 1.0 |
| Polyquaternium-22 (Merquat 295) | 0.2 | — | 0.2 | — | 0.2 | — |
| Polyquaternium-37 & Mineral Oil (Salcare SC95) | 0.2 | — | 0.2 | — | 0.2 | — |
| Styrene-PVP Copolymer (Polectron 430) | 0.1 | 0.5 | 0.1 | 0.5 | 0.1 | 0.5 |
| Xanthan Gum | 0.1 | — | 0.1 | — | 0.1 | — |
| Acrylates/C10-30 Alkyl Acrylate Crosspolymer | — | 0.5 | — | 0.5 | — | 0.5 |
| Cetyl Alcohol | 2.0 | — | 2.0 | — | 2.0 | — |
| Acrylates Steareth-20 Methacrylate Copolymer (Aculyn 22) | 0 | 1.0 | 0 | 1.0 | 0 | 1.0 |
| Acrylates copolymer (Aculyn 33) | 1.0 | 1.0 | 1.0 | 1.0 | 1.0 | 1.0 |
| Steareth-200 | 1.0 | 1.0 | 1.0 | 1.0 | 1.0 | 1.0 |
| Propylene Glycol | 3.0 | 3.0 | 3.0 | 3.0 | 3.0 | 3.0 |
| Diethylene-triamine-penta(methylene phosphonic) acid | 0.5 | 1.0 | 0.5 | 1.0 | — | — |
| Ethylene Diamine Di Succinate | — | — | 1.0 | 3.0 | 1.0 | 3.0 |
| p-Phenylenediamine | 0.6 | 0.6 | 0.6 | 0.6 | 0.6 | 0.6 |

-continued

| | 25 | 26 | 27 | 28 | 29 | 30 |
|---|---|---|---|---|---|---|
| 4-Amino-2-hydroxytoluene | 0.6 | 0.6 | 0.6 | 0.6 | 0.6 | 0.6 |
| p-Aminophenol | 0.25 | 0.25 | 0.25 | 0.25 | 0.25 | 0.25 |
| 1-Naphthol | 0.3 | 0.3 | 0.3 | 0.3 | 0.3 | 0.3 |
| Resorcinol | 0.2 | 0.2 | 0.2 | 0.2 | 0.2 | 0.2 |
| 2-methyl resorcinol | 0.1 | 0.1 | 0.1 | 0.1 | 0.1 | 0.1 |
| m-aminophenol | 0.4 | 0.4 | 0.4 | 0.4 | 0.4 | 0.4 |
| 3-amino-2,6-dimethyl phenol | 0.2 | 0.2 | 0.2 | 0 | 0 | 0 |
| 2-methyl-5-hydroxyethylaminophenol | 0.2 | 0.2 | 0.2 | 0.2 | 0.2 | 0.2 |
| 1-acetoxy-2-methylnaphthalene | 0.3 | 0.3 | 0.3 | 0.3 | 0.3 | 0.30 |
| 2-amino-3-hydroxypyridine | 0.0 | 0.1 | 0.0 | 0.1 | 0.0 | 0.3 |
| 2-amino-4-hydroxyethylaminoanisole | 0.1 | 0.1 | 0 | 0 | 0 | 0 |
| Phenyl methyl pyrazolone | 0.1 | 0.1 | 0.1 | 0.1 | 0.1 | 0.1 |
| 4-chlororesorcinol | 0.1 | 0.1 | 0.1 | 0.1 | 0.1 | 0.1 |
| 1,3-bis(2,4-diaminophenoxy)propane HCl | 0 | 0 | 0.1 | 0.1 | 0 | 0 |
| 5-Amino-6-chloro-o-cresol | 0.05 | 0.05 | 0.05 | 0.05 | 0.05 | 0.05 |
| 5-Amino-4-chloro-o-cresol | 0 | 0 | 0 | 0.2 | 0.2 | 0.2 |
| 6-Methoxy-2-methylamino-3-aminopyridine HCl | 0 | 0 | 0 | 0 | 0.1 | 0.1 |
| 2,6-Dimethoxy-3,5-Pyridinediamine HCl | 0 | 0 | 0 | 0 | 0.1 | 0.1 |
| Hydroxyethyl-2-Nitro-p-Toluidine | 0.1 | 0.1 | 0.1 | 0 | 0 | 0 |
| 2-amino-4,6-dinitrophenol | 0.1 | 0.1 | 0.1 | 0 | 0 | 0 |
| 3-nitro-p-hydroxyethylaminophenol | 0 | 0 | 0 | 0.1 | 0.1 | 0.1 |
| 4-hydroxypropylamino-3-nitrophenol | 0 | 0 | 0 | 0.1 | 0.1 | 0.1 |
| pH adjust to pH 9.0 | qs | qs | qs | qs | qs | qs |
| Water | qs | qs | qs | qs | qs | qs |

Test Data

The specified dye couples were formulated into the exemplified colour chassis (below) at a concentration of 0.02M having a primary intermediate (developer):coupler ratio of 1:1, but with no other dye species present. The formulation was made by first making a 40% concentrated emulsion base with the surfactants and fatty alcohols. To make this base the surfactants and fatty alcohols were melted in deionised water at 85° C. The mixture was then cooled to 60° C., where it was milled at 4000 rpm with a Turrax T50 before cooling to room temperature. The dyes, stabilizers and solvent were then added and thoroughly mixed with the emulsion base until homogeneous. Either a control level of 0.025% EDTA was used or 0.025% EDTA+1.0% DTPMP chelant was added. The final dye composition was mixed in a 1:1 ratio with hydrogen peroxide composition (formulation I) and then the mixture was applied to the hair at a ratio of 4 g of product to 1 g of hair. After leaving the colour to develop for 30 minutes the hair was rinsed for one minute and then the colour measured using a 3700d Minolta Spectrophotometer. The substrate used was natural white unpigmented hair that had been colored for 5 repeat cycles with a commercial coloring product (extra light blonde shade). In between each coloring cycle the hair was shampooed twelve times with a commercial clarifying shampoo. This substrate was used to represent the substrate of consumers that are regular users of coloring products.

For wash fading, the substrate was washed for a total of three complete washing cycles where each cycle consisted of two shampoo treatments and one conditioner treatment followed by blow drying until dry. Color measurements were made after three wash cycles using a Minolta CM3700d spectrophotometer. The difference in color for the formulation with no DTPMP chelant was compared to that with the DTPMP chelant and the color difference (dE) value calculated according to the equation:

$$dE = [(dL)^2 + (da)^2 + (db)^2]^{1/2}$$

A dE of 2 is considered as indicative of what would be noticeable by the consumer as being a different colour. The dL number is also significant as it is a measure of the lightness of the colour. A lower L value means the color is darker and more intense.

Table 1 shows the results for five selected primary intermediate (developer)-coupler combinations utilized in the formulations given below. The control contains no amino-phosphonate chelant, only 0.025% EDTA.

Formulations

Emulsion Base Premix Ingredients

1. Protocol

| 1 | Add cold water and commence agitation |
|---|---|
| 2 | Heat water to 82 C. |
| 3 | Add EDTA, Na Benzoate, Ceteareth-25 |
| 4 | Add Stearyl/Cetyl Alcohol and Phenoxyethanol |
| 5 | Hold for 45 Mins at 80 C. |
| 6 | Cool to 60 C. whilst milling at 4000 rpm using Turrax T50 |
| 7 | At 60 C., stop milling and continue cooling to 50 C. |
| 8 | Hold at 50 C. for 1 hour |
| 9 | Allow to cool to 30 C. |

2. Ingredients

| Description | Wt % |
|---|---|
| DI Water | 82.6833 |
| Cetyl Alcohol | 6.2500 |
| Stearyl Alcohol | 6.2500 |
| Ceteareth 25 | 4.1667 |
| Phenoxyethanol | 0.3000 |
| Sodium Benzoate | 0.2500 |
| Tetra Sodium EDTA | 0.1000 |

Formulation of the Dye-Composition:

1. Protocol

| | |
|---|---|
| 1 | Add cold water and commence agitation |
| 2 | Add EDTA, sodium sulfite & ascorbic acid |
| 3 | Add propylene glycol |
| 4 | Add dye precursors |
| 5 | Stir for 15 minutes |
| 6 | Weigh out emulsion base in separate container |
| 7 | Add dye mix slowly to emulsion base with stirring |
| 8 | Stir until homogeneous |
| 9 | Add either DI water or Chelant according to formulation required |
| 10 | Stir until homogeneous |

2. Ingredients

| Description | Wt % |
|---|---|
| DI Water | Qs |
| Na2EDTA | 0.0500 |
| Sodium sulfite | 0.2000 |
| Ascorbic acid | 0.2000 |
| Propylene glycol | 0.0500 |
| Developer | 0.02M |
| Coupler | 0.02M |
| Emulsion base | 40.0000 |
| Chelant | 10.0000 |

Developer Formulation I

| Dye Combination | L | a | b | dL vs control | dE vs control |
|---|---|---|---|---|---|
| After Colouring | | | | | |
| PPD-AHT Control | 30.889 | 20.204 | −1.425 | | |
| PPD-AHT + 1.00% DTPMP | 27.815 | 20.295 | −1.830 | 3.07 | 3.10 |
| PPD-AHT + 0.50% DTPMP | 27.158 | 19.579 | −1.283 | 3.73 | 3.79 |
| PPD-AHT + 0.25% DTPMP | 27.085 | 20.050 | −1.474 | 3.81 | 3.81 |
| PPD-DAPE Control | 30.325 | −0.499 | −4.631 | | |
| PPD-DAPE + 1.00% DTPMP | 28.255 | 1.003 | −7.703 | 2.07 | 4.00 |
| HED-Napthol | 33.213 | −3.579 | −15.217 | | |
| HED-Napthol + 1.00% DTPMP | 26.619 | −0.780 | −18.312 | 6.59 | 7.80 |
| PPD-HBM Control | 47.063 | 3.432 | 12.295 | | |
| PPD-HBM + 1.00% DTPMP | 44.117 | 4.430 | 12.655 | 2.95 | 3.13 |
| PAP-PAOX Control | 55.333 | 22.035 | 27.837 | | |
| PAP-PAOX + 1.00% DTPMP | 48.866 | 26.694 | 29.869 | 6.47 | 8.23 |
| After Wash Cycles | | | | | |
| PPD-AHT Control | 37.389 | 18.302 | 0.726 | | |
| PPD-AHT + 1.00% DTPMP | 35.548 | 18.119 | −0.132 | 1.84 | 2.04 |
| PPD-AHT + 0.50% DTPMP | 32.538 | 18.953 | −0.095 | 4.85 | 4.96 |
| PPD-AHT + 0.25% DTPMP | 34.257 | 18.156 | 0.075 | 3.13 | 3.20 |
| PPD-DAPE Control | 37.210 | −0.354 | 0.026 | | |
| PPD-DAPE + 1.00% DTPMP | 32.823 | 0.879 | −4.062 | 4.39 | 6.12 |
| HED-Napthol | 40.431 | −6.245 | −14.267 | | |
| HED-Napthol + 1.00% DTPMP | 31.283 | −2.004 | −22.711 | 9.15 | 13.15 |
| PPD-HBM Control | 51.211 | 2.758 | 11.194 | | |
| PPD-HBM + 1.00% DTPMP | 46.787 | 4.265 | 11.724 | 4.42 | 4.70 |
| PAP-PAOX Control | 61.969 | 16.702 | 24.823 | | |
| PAP-PAOX + 1.00% DTPMP | 56.842 | 22.328 | 28.496 | 5.13 | 8.45 |

Colours obtained from the dye combinations
p-phenylene diamine (PPD)-4-Amino-2-Hydroxytoluene (AHT); Purple
p-phenylene diamine (PPD)-2,4-diaminophenoxyethanol dihydrochloride (DAPE); Blue/Grey
N,N-bis(2-hydroxyethyl)-p-phenylenediamine sulfate (HED)-1-Napthol (Napthol); Blue
p-phenylene diamine (PPD)-Hydroxybenzomorpholine (HBM); Brown
p-amino phenol (PAP)-2-methyl-5-hydroxyethylaminophenol (PAOX); Orange It was observed that the dye colour developed significantly slower when the dye base was applied to hair for all the formulations that contained the DTPMP chelant.

After rinsing for one minute the hair treated with the amino phosphonic acid type chelant-containing formulations were all significantly darker than the control with no added chelant. This data confirms that more dye has been deposited inside the hair.

Consequently, these results demonstrate that the consumer will observe an increased tonality to the shade and better wash fastness of the tone over time.

The dimensions and values disclosed herein are not to be understood as being strictly limited to the exact numerical values recited. Instead, unless otherwise specified, each such dimension is intended to mean both the recited value and a functionally equivalent range dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair colouring composition comprising
   a) an oxidizing agent
   b) at least one primary intermediate (developer) hair dye and at least one coupler dye selected from the group consisting of 4-amino-2-hydroxytoluene, 2-methyl-5-hydroxyethylaminophenol, 2,4-diaminophenoxyethanol, 6-hydroxybenzomorpholine, 1-napthol and mixtures thereof and
   c) diethylene-triamine-penta-(methylenephosphonic acid).

2. A composition according to claim 1 wherein said composition comprises from about 0.1% to about 5% of diethylene-triamine-penta-(methylenephosphonic acid).

3. A composition according to claim 1, further comprising an additional chelant.

4. A composition according to claim 1 comprising from about 0.1% to about 10% of said oxidizing agent, from about 0.001% to about 5% of said primary intermediate (developer) and from about 0.001% to about 5% of said coupler.

5. A composition according to claim 1, wherein said primary intermediate (developer) is selected from the group consisting of methoxymethyl-p-phenylenediamine, 2,6-dichloro-4-aminophenol, 5-amino-2-ethyl-phenol, 2,5-toluenediamine sulphate, N-phenyl-p-phenylenediamine, p-phenyldiamine, p-methylaminophenol, N,N-bis(2-hydroxyethyl)-p-phenylenediamine, 3-methyl-p-minophenol, hydroxyethyl-p-phenylenediamine, hydroxypropyl bis(N-hydroxyethyl)-p-phenylenediamine, 1-hydroxyethyl 4,5-diamino pyrazole, 2,2'-methylenebis-4-aminophenol, 5-methyl-orthoaminophenol, 5-ethyl-orthoaminophenol and mixtures thereof.

6. A composition according to claim 1 wherein said composition further comprises a peroxymonocarbonate ion source.

7. A composition according to claim 6, wherein said composition further comprises an alkalizing agent and wherein said composition has a pH of up to and including about pH 9.5.

8. A composition according to claim 1, further comprising a gel network thickening system comprising at least one surfactant or amphophile having an HLB of 6 or less selected from fatty alcohols comprising from 14 to 30 carbon atoms, at least one anionic surfactant selected from C8-C30 alkyl ether phosphates having from 1 to 20 ethylene oxide units, and at least one non-ionic surfactant having an HLB of 7 or more selected from polyoxyethylene alkyl ethers having at least 25 ethylene oxide units.

9. A method of treating hair comprising the steps of contacting the hair with a composition according to claim 1, and subsequently removing said composition from the hair.

10. A method of treating hair comprising the subsequent steps of:
  i) contacting hair with a first composition comprising:
    a) diethylene-triamine-penta-(methylenephosphonic acid);
  ii) contacting hair immediately after step i) with a second composition comprising an oxidizing agent, a primary intermediate (developer) dye, and at least one coupler dye selected from the group consisting of 4-amino-2-hydroxytoluene, 2-methyl-5-hydroxyethylaminophenol, 2,4-diaminophenoxyethanol, 6-hydroxybenzomorpholine, 1-napthol and mixtures thereof.

11. A hair colouring kit comprising
  i) an individually packaged oxidizing component comprising an oxidizing agent and
  ii) an individual packaged second component comprising at least one primary intermediate (developer) hair dye, at least one coupler dye selected from the group consisting of 4-amino-2-hydroxytoluene, 2-methyl-5-hydroxyethylaminophenol, 2,4-diaminophenoxyethanol, 6-hydroxybenzomorpholine, 1-napthol and mixtures thereof, and
diethylene-triamine-penta-(methylenephosphonic acid).

* * * * *